United States Patent
Edwards et al.

(10) Patent No.: US 6,355,441 B1
(45) Date of Patent: Mar. 12, 2002

(54) BENZOTHIAZOLE DIOXETANES

(75) Inventors: Brooks Edwards, Cambridge; Irena Bronstein, Newton, both of MA (US)

(73) Assignee: Tropix, Inc., Bedford, MA (US)

( * ) Notice: Subject to any disclaimer, the term of this patent is extended or adjusted under 35 U.S.C. 154(b) by 0 days.

(21) Appl. No.: 09/362,047

(22) Filed: Jul. 28, 1999

Related U.S. Application Data

(60) Provisional application No. 60/094,336, filed on Jul. 28, 1998.

(51) Int. Cl.[7] .............................................. G01N 33/53
(52) U.S. Cl. .......................... 435/7.1; 435/7.4; 435/6; 549/332; 549/264; 530/331; 530/330; 530/807; 548/526
(58) Field of Search ..................... 435/7.4, 7.1, 6; 549/332, 264; 530/331, 807, 330; 548/526

(56) References Cited

U.S. PATENT DOCUMENTS

| | | | |
|---|---|---|---|
| 4,978,614 A | * | 12/1990 | Bronstein |
| 5,326,882 A | * | 7/1994 | Bronstein et al. |
| 5,591,591 A | * | 1/1997 | Bronstein et al. |
| 5,679,802 A | | 10/1997 | Bronstein et al. |
| 5,679,803 A | * | 10/1997 | Bronstein et al. |
| 5,753,436 A | * | 5/1998 | Bronstein et al. |
| 5,763,681 A | * | 6/1998 | Edwards et al. |
| 5,840,919 A | * | 11/1998 | Bronstein et al. |
| 5,843,681 A | * | 12/1998 | Bronstein et al. |
| 5,981,768 A | * | 11/1999 | Bronstein et al. |

FOREIGN PATENT DOCUMENTS

| | | | |
|---|---|---|---|
| EP | 0348491 | * | 8/1994 |
| EP | 0387342 | * | 8/1995 |
| EP | 0416038 | * | 3/1997 |
| EP | 0629195 | * | 5/1999 |
| WO | 96/25667 | * | 8/1996 |

OTHER PUBLICATIONS

Edwards et al., J. Biolumin. chemilumin., 5, 1–4, 1990.*
Kobos et al., Analytical Biochemistry, 224, 128–133, 1995.*
Martin et al., Biolumin. Chemilumin., Proc. Int. Symp., 9th, 525–528, 1997.*
Olesen et al., Methods in Enzymology, 305:417–427, 2000.*
Thorpe et al., Clin. Chem., 35(12), 2319–2321, 1989.*
Voyta et al., biolumin. Chemilumin., Proc. Int. Symp., 9th, 529–532, 1997.*
Bronstein et al., J. Biolumin. Chemilumin., 44, 99–111, 1989.*
Bronstein et al., Properties of 1,2–dioxetane Chemiluminescence. 168–175, 2000.*
Bronstein et al., Clin. Chem. 42(9), 1542–1546, 1996.*
Edwards et al., J. Org. Chem., 55, 6225–6229, 1990.*
Adam et al., J. Am. Chem., Soc., 118, 10400–10407, 1996.*
Adam et a., J. Phys. Chem., 102, 5406–5414, 1998.*
Adam et al., J. am. Chem. Soc., 121, 958–961, 1999.*
Adam et al., Biolumin. chemilumin, Proc. Int. Symp., 10th, 33–36, 1999.*

* cited by examiner

*Primary Examiner*—Bao-Thuy L. Nguyen
(74) *Attorney, Agent, or Firm*—Piper Marbury Rudnick & Wolfe LLP; Steven B. Kelber

(57) ABSTRACT

Chemiluminescent 1,2-dioxetane compounds capable of producing light energy when decomposed, substantially stable at room temperature, represented by the formulas I or II:

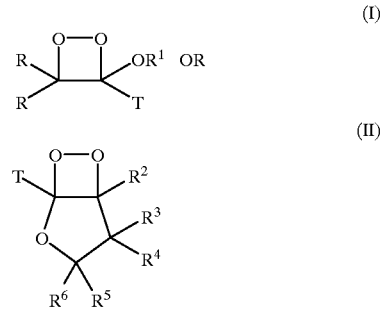

wherein T is:

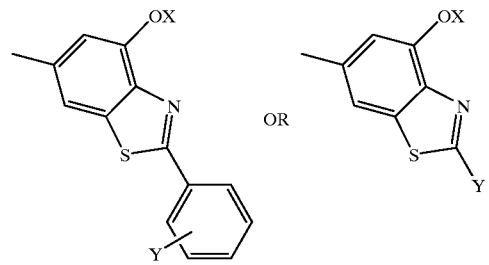

20 Claims, 17 Drawing Sheets

FUSED(HETEROARYL)BENZOTHIAZOLE
1,2-DIOXETANE PHOSPHATE

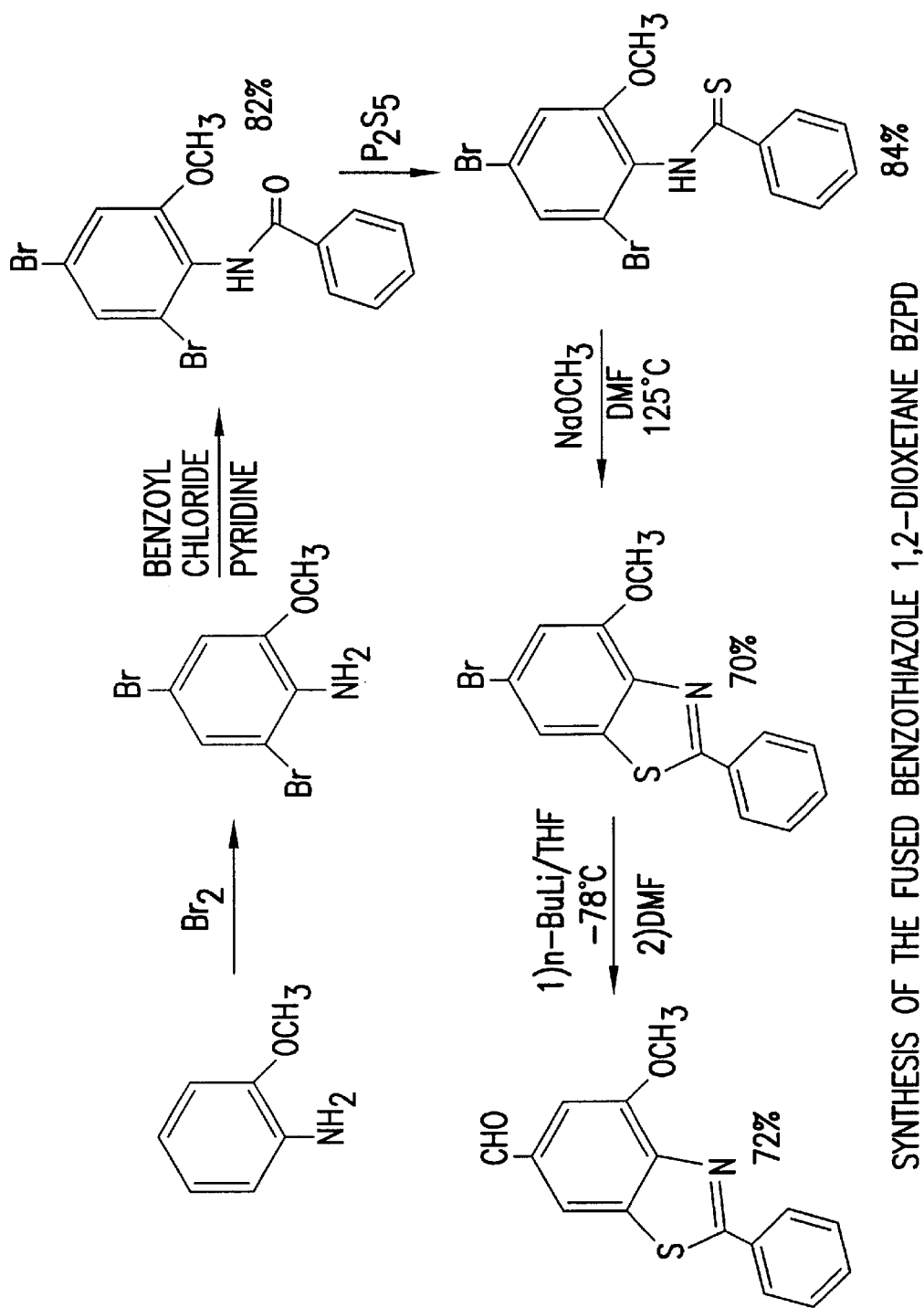
FIG.2A SYNTHESIS OF THE FUSED BENZOTHIAZOLE 1,2-DIOXETANE BZPD

PHOTOXYGENATION OF BENZOTHIAZOLE
ENOL ETHER PHOSPHATE

BENZYLOXY ENOL ETHER DERIVATIVES ALLOW REGIOSELECTIVE LIBERATION OF A PHENOL TO CREATE A LINKABLE GREEN-EMITTING SYSTEM

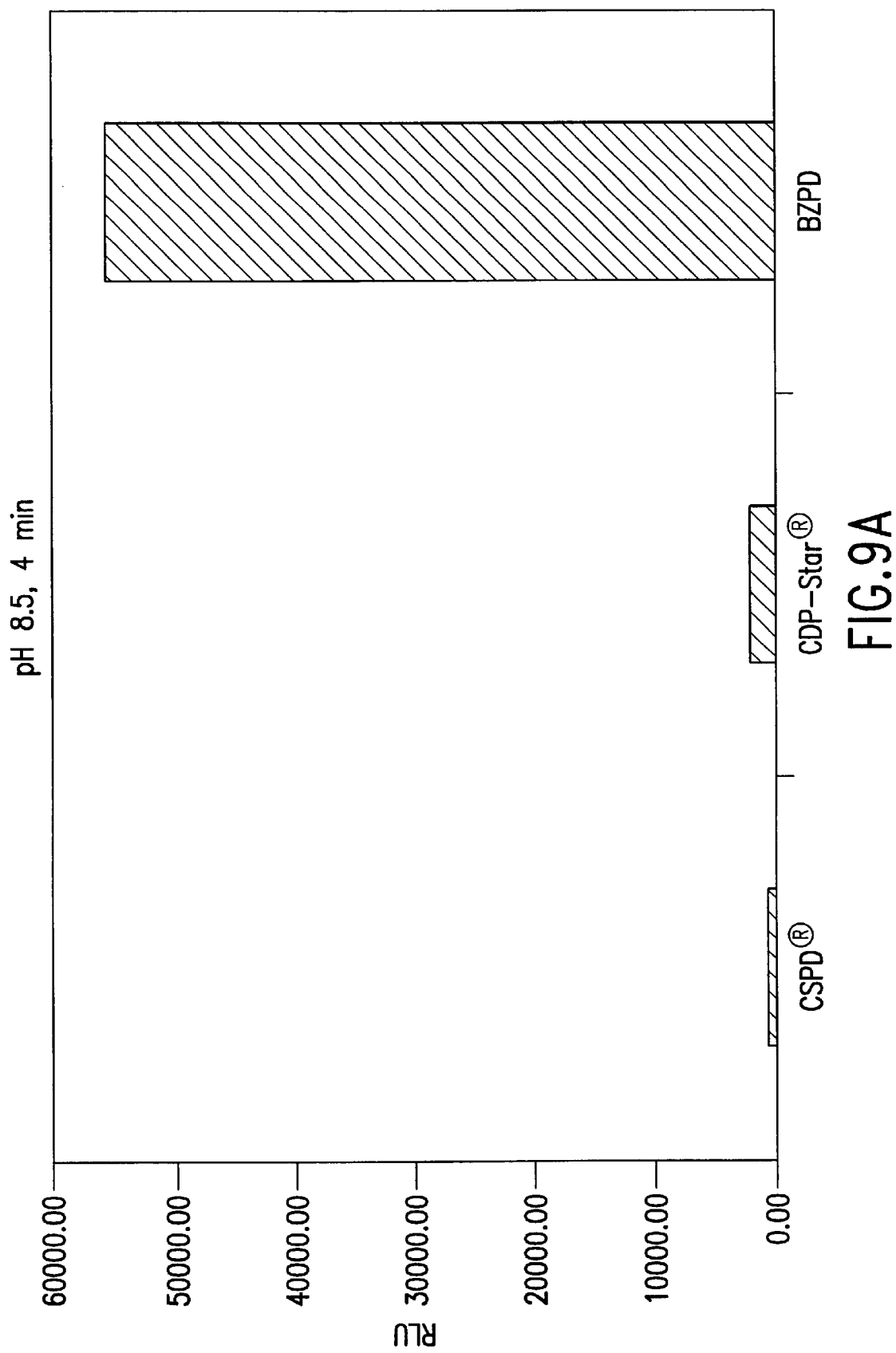

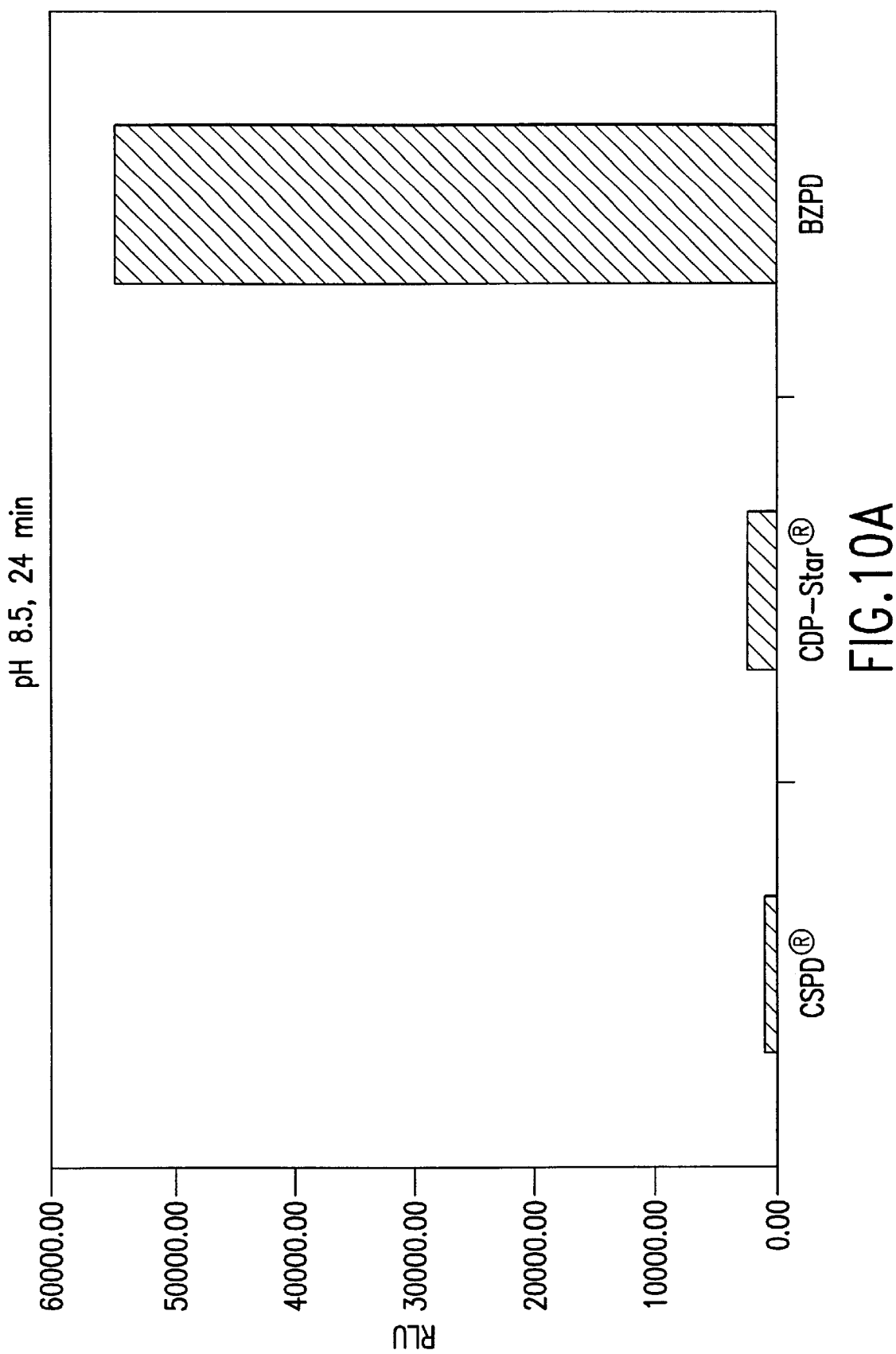

BENZOTHIAZOLE DIOXETANES

This application is a regular National application claiming priority from Provisional Application, U.S. application Ser. No. 60/094,336 filed Jul. 28, 1998. The entirety of that provisional application is incorporated herein by reference.

BACKGROUND OF THE INVENTION

Field of the Invention

This invention relates to improved chemiluminescent 1,2-dioxetane compounds. More particularly, this invention relates to improved enzymatically cleavable chemiluminescent 1,2-dioxetane compounds that contain enzymatically removable labile groups. Such labile groups prevent the molecule from decomposing to produce light, i.e visible light or light detectable by appropriate instrumentation, until an appropriate enzyme is added to remove the labile group.

One enzyme molecule can affect the removal, through a catalytic cycle, of its complimentary labile group from thousands of enzymatically cleavable chemiluminescent 1,2-dioxetane molecules. This is a marked contrast to the situation with chemically cleavable chemiluminescent 1,2-dioxetanes, where one molecule of chemical cleaving agent is needed to remove the complimentary labile group from each dioxetane molecule.

Enzymatically cleavable light-producing 1,2-dioxetane compounds will usually also contain stabilizing groups, such as an adamantylidene group spiro bonded to the dioxetane ring's 3-carbon atom, that will aid in preventing the dioxetane compound from undergoing spontaneous decomposition at room temperature (about 25° C.) before the bond by which the enzymatically cleavable labile group is attached to the remainder of the molecule is intentionally cleaved. Wierynga, et al., *Tetrahedron Letters*, 169 (1972), and McCapra, et al., J. Chem. Soc., Chem. Comm., 944 (1977). These stabilizing groups thus permit such dioxetanes to be stored for exceptionally long periods of time before use, e.g., for from about 12 months to as much as about 12 years at temperatures ranging from about 4° C. to about as much as 30° C. without undergoing substantial decomposition.

This invention further relates to the incorporation of its dioxetane molecules in art-recognized immunoassays, chemical assays and nucleic acid probe assays, and to their use as direct chemical/physical probes for studying the molecular structure or micro structures of various micro molecules, synthetic polymers, proteins, nucleic acids, catalytic antibodies, and the like, to permit an analyte-to chemical or biological substance whose presence, amount or structure is being determined to be identified or quantified.

Background of the Invention

Applications naming one or more of the inventors herein, as inventors, and assigned to Tropix, Inc., have clearly established 1,2-dioxetanes as chemiluminescent compounds which can be used as reporters and labels in ultra sensitive assays that can be conducted quickly, without resort to exotic conditions or elaborate apparatus, for the detection of a variety of biological materials. Among these are U.S. Pat. Nos. 4,931,223; 4,931,569; 4,952,707; 4,956,477; 4,978,614; 5,032,381; 5,145,772; 5,220,005; 5,225,584; 5,326,882; 5,330,900; 5,336,596; and 5,871,938. All of the foregoing are incorporated herein by reference. Other patents commonly assigned with this application have issued, and other applications are pending. Together this wealth of patent literature addresses 1,2-dioxetanes, stabilized by a typically polycyclic group, such as spiroadamantane bonded to one of the carbons of the dioxetane ring, and a moiety bonded to the remainder carbon of the dioxetane ring which is electron sensitive, such that the protection of the electron sensitive moiety, typically an aryl group, leads to an anion, generally an oxyanion, which is unstable, and decomposes. Through decomposition, the 0—0 bond is broken and a photon is generated. The same carbon atom to which this electron sensitive moiety is bonded may bear an alkoxy or other electron-active group.

The first of the dioxetanes of this class commercialized was 3-(4-methoxy-spiro(1,2-dioxetane-3,2'-tricyclo (3.3.1.1$^{3,7}$) decan)-4-yl)phenyl phosphate, particularly the disodium salt, generally known as AMPPD®. This compound has been commercialized by assignee of this application, Tropix, Inc., as well as a company of Detroit, Mich., Lumigen, Inc. Superior performance of the above described compounds can be obtained by selective substitution on the spiroadamantane ring. Substitution, at either bridgehead carbon with an electron active species, such as chlorine, improves reaction speed and signal to noise ratio (s/n). The chlorine substituted counterpart of AMPPD®, CSPD®, has been widely commercialized by Tropix, Inc. of Bedford, Mass. "Third-generation" dioxetane compounds of similar structure, wherein the aryl moiety also bears an electron active substituent, such as chlorine, offer further improvements in performance, and have been commercialized by Tropix, Inc. The phosphate moieties are available under the trademarks CDP® and CDP-Star®.

However, it has been observed that AMPPD® in aqueous solution, and also in the presence of chemiluminescent enhancers, e.g., a polymeric ammonium, phosphonium or sulphonium salt such as poly[vinyl benzothiazole (benzothiazole dimethyl ammonium chloride)] ("BDMQ") and other hetero polar polymers may exhibit longer than optimum periods of time to reach constant light emission characteristics ("t ½", defined as the time necessary to obtain one-half of the maximum chemiluminescence intensity at constant, steady-state light emission levels; this emission half-life varies as a function of the stability of the dioxetane oxyanion in various environments).

Statistically, approximately seven t ½ periods are required to reach steady-light emission kinetics. The t ½ of AMPPD® at concentrations above $2\times10^{-5}$ M in an aqueous solution at pH 9.5 in the presence of BDMQ have been found to be 7.5 minutes. At $4\times10^{-3}$ M in the absence of BDMQ, the t ½ has been found to be approximately 30–60 minutes, while at $2\times10^{-5}$ M in an aqueous solution, the t ½ for AMPPD® has been found to be 2.5 minutes.

In rapid bioassays that employ enzymatically cleavable chemiluminescent 1,2-dioxetanes as reporter molecules, it is desirable to reach steady-state light emission kinetics as quickly as possible so as to detect an "endpoint" in the assay. While chemiluminescent intensity can be measured before achieving steady state kinetics, sophisticated, thermally controlled luminometry instrumentation must be used if one wishes to acquire precise data prior to steady-state emission kinetics.

Furthermore, AMPPD®, in an aqueous buffered solution both in the presence and absence of chemiluminescent enhancers such as BDMQ, exhibits higher than desirable thermal and non-enzymatically activated light emission, or "noise". Such noise can be attributed to emission from the excited state adamantanone and of the methyl m-oxybenzoate anion derived from the aromatic portion of the AMPPD® molecule. This noise can limit the levels of detection, and thus prevent the realization of ultimate sensitivity, as the measured noise level of AMPPD® is approximately two orders of magnitude above the dark current in a standard luminometer.

Importantly, various instruments for detecting chemiluminescent emission such as CCD cameras have greater detection sensitivities in the green and red wavelengths. AMPPD® and related dioxetanes typically emit in the blue wavelengths of the visible spectrum. Heretofore it has been necessary to use polymeric enhancers to "shift" the emission wavelength. It would be desirable to obtain dioxetanes which emit in wavelengths closer to the "red or green end" of the visible spectrum, to enhance detection sensitivity.

It is, therefore, an object of this invention to decrease the time necessary to conduct assays, and particularly bioassays, in which enzymatically cleavable chemiluminescent 1,2-dioxetanes are used as reporter molecules.

It is also an object of this invention to provide new and improved enzymatically cleavable chemiluminescent 1,2-dioxetanes which, when used as reporter molecules in assays, and in particular bioassays, reduce the time required to complete the assay.

A further object of this invention is to provide a new and improved enzymatically cleavable chemiluminescent 1,2-dioxetane for use as substrates for enzyme-based assays, and particularly bioassays, which provide improved signal to background behavior and thus provide improved detection levels.

A further object of this invention is the provision of dioxetane whose emission wavelengths are shifted toward the green and red wavelengths.

A still further object of this invention is to provide novel intermediates useful in synthesizing these improved enzymatically cleavable 1,2-dioxetanes.

Another object of this invention is to provide methods of preparing these enzymatically cleavable chemiluminescent 1,2-dioxetanes and intermediates thereof.

These and other objects, as well as the nature, scope and utilization of this invention, will become readily apparent to those skilled in the art from the following description and the appended claims.

SUMMARY OF THE INVENTION

The above objects, and others, made clear by the discussion set forth below, is met by a new family of dioxetanes of the general formula(s):

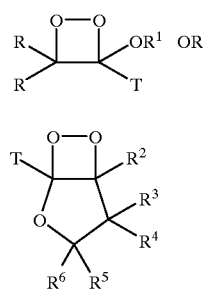

wherein T is:

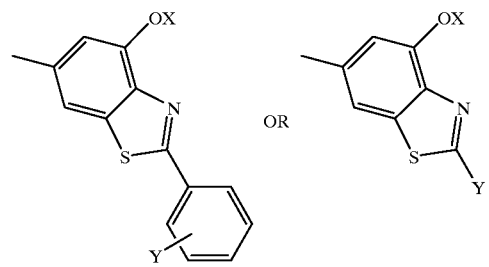

wherein each R may independently be any branched alkyl or cycloalkyl group which provides stabilization for the dioxetane, or both R groups may be joined in a cycloalkyl or polycycloalkyl moiety Spiro bound to the dioxetane ring wherein the R group or groups may be unsubstituted or substituted with a halogen atom, an alkoxy group, or an electron-withdrawing organic group, and wherein $R^1$ is an aryl group, or an alkyl group of 1–20 carbon atoms, which may be optionally substituted with 1 or more halogen atoms, and wherein Y may be H, or an electron donating or withdrawing group, or an organic linker group attached to an ancillary fluorophore, or to any biological moiety, and wherein X may be any protecting group which is removable by chemical or enzymatic means, wherein $R^2$–$R^6$ are independently H, alkyl, or branched alkyl, substituted alkyl, aryl, substituted aryl, wherein $R^3$ and $R^4$ may be joined as a spiro-fused cycloalkyl group.

The above dioxetanes may be synthesized by way of the fused benzothiazole aldehyde, or toluene derivative using permanganate oxidation to provide a carboxylic acid. Esters of this acid may be used to prepare dioxetane precursors for the above compounds according to methodology described in U.S. Pat. No. 5,731,445 which is incorporated herein by reference.

BRIEF DESCRIPTION OF THE DRAWINGS

FIGS. 9A–B illustrate the speed of chemiluminescent kinetics, and sensitivity, of the inventive dioxetanes as opposed to commercial prior art dioxetanes.

DETAILED DESCRIPTION

Figure 1:
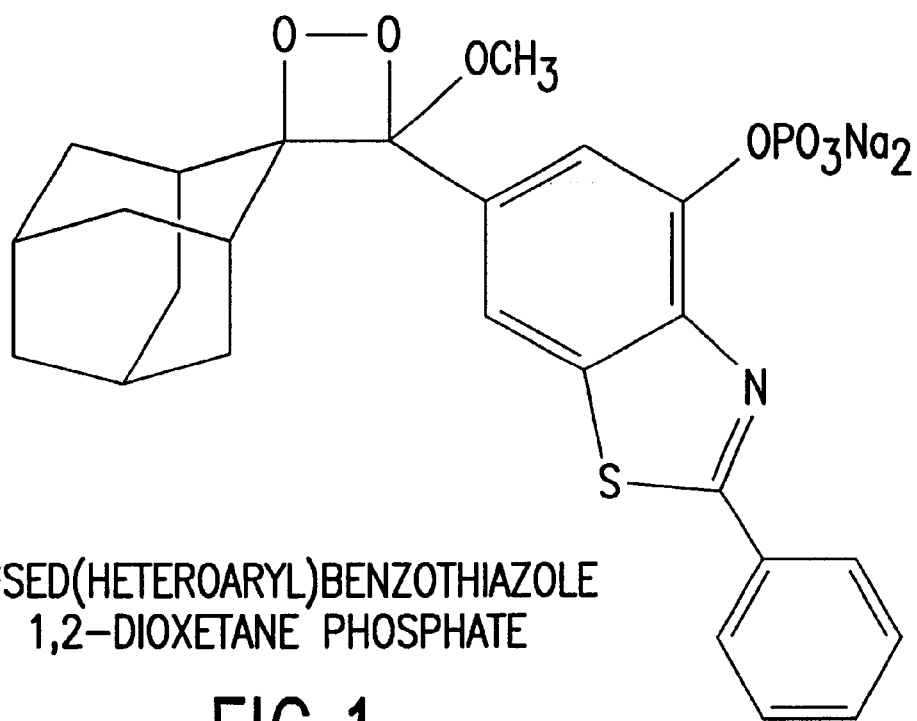
FIG. 1 shows a fused(heteroaryl)benzothiazole 1,2-dioxetane phosphate.

We now describe the structure, synthesis, and use of preferred embodiments of the present invention.

Structure

The invention employs dioxanes having the general formula(s):

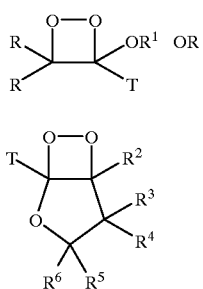

wherein T is:

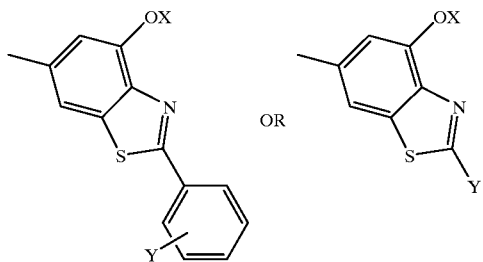

wherein each R may independently be any branched alkyl or cycloalkyl group which provides stabilization for the dioxetane, or where both R groups together form a cycloalkyl or polycycloalkyl moiety spiro bound to the dioxetane ring wherein each R or the spiro bound cyclic group may be unsubstituted or substituted with a halogen atom, an alkoxy group, or an electron-withdrawing organic group, and wherein $R^1$ is an aryl group, or an alkyl group of 1–20 carbon atoms, which may be optionally substituted with 1 or more halogen atoms, and wherein Y may be H, or an electron donating or withdrawing group, or an organic linker group which may be attached to an ancillary fluorophore or to any biological moiety, and wherein X may be any protecting group which is removed by chemical or enzymatic means, wherein $R^2$–$R^6$ are independently H, alkyl, substituted alkyl, aryl, substituted aryl, wherein $R^3$ and $R^4$ may be joined as a spiro-fused cycloalkyl group.

Representative identities for each of the substituents of formulas I and II will be familiar to those of skill in the art, given the novel chemical formulas herein, and the earlier patents of Tropix incorporated herein by reference. Preferred identities for R include straight or branched chain alkyls of 2–12 carbon atoms, with a preference for branched alkyl groups. Each alkyl group may be substituted with one or more electron-withdrawing or electron-donating groups, and/or each alkyl moiety R may be substituted with one or more groups which increase the solubility of the overall dioxetane, which is generally quite hydrophobic. Preferred solubilizing groups include carboxylic acid moieties, sulfonic acid moieties, phosphoric acid moieties, trifluoromethyl moieties, etc.

In a preferred embodiment, both R groups together form a spiroadamantyl group, which may be unsubstituted, or substituted at either head carbon, or both, with an electron active (electron withdrawing or electron donating) group, including alkoxy of 1–7 carbon atoms, halo, alkyl, etc. Exemplary substituents on the adamantyl group are set forth in U.S. Pat. No. 5,112,960, incorporated herein by reference. Beyond spiroadamantyl groups, the identity of each group R is selected so as to provide steric stablization for the dioxetane, to prevent premature decomposition.

$R^2$–$R^6$ are each independently selected, save that $R^3$ and $R^4$ may be joined to form a spiro-fused cycloalkyl group, as described above for groups R. Otherwise, $R^2$–$R^6$ are independently selected from hydrogen, alkyl unsubstituted or substituted with one or more halogen groups, particularly fluorine, such as trifluoroalkyl of 1–6 carbon atoms, hydroxy, phenyl, naphthyl, etc. Each and/or all, or any combination, of moieties $R^2$–$R^6$ may be further substituted with groups calculated to enhance the water solubility of the dioxetane, as described above. Each moiety $R^2$–$R^6$ may bear one or two water solubility-enhancing groups. Instead of alkyl, each and/or all of $R^2$–$R^6$ may be aryl, preferably phenyl.

Substituent Y may serve one or more functions. Y may be hydrogen, or, to effect the decomposition kinetics of the unprotected dioxetane (see the identities for X, below) Y may be an electron withdrawing group (e.g., any heteroaryl group). Y may be an electron donating group (e.g., any alkyl group). Additionally, a wide variety of other electron-active substitutents for substitution on aryl moieties for dioxetanes are set forth for the substituent "Z" in U.S. Pat. No. 5,538,847, incorporated herein by reference. Thus Y can be selected from a wide variety of identities. Preferred electron-active substituents include chloro, alkoxy (—OR), aryloxy (—OAr), trialkylammonium (—NR$_3$+), alkylamido (—NHCOR, —NRCOR'), arylamido (NHCOAr, —NRCOAr, —NarCOAr), arylcarbamoyl (—NHCOOAr, —NRCOOAr), alkylcarbamoyl (NHCOOR, —NRCOOR'), cyano (—CN), nitro (—NO$_2$), ester (—COOR, —COOAr), alkyl- or arylsulfonamido (—NHSO$_2$R, —NHSO$_2$Ar), trifluoromethyl (—CF$_3$), aryl (—Ar), alkyo (—R), trialkyl-, triaryl-, or alkylarysilyl (—SiR$_3$, SiAr$_3$, —SiArR$_2$), alkyl- or arylamido sulfonyl (SO$_2$NHCOR, —SO$_2$NHCOAr), alkyl or aryl sulfonyl (—SO$_2$R, SORAr) alkyl- or arylthio ethers (—SR, Sar). The size of the Z substituent is generally limited only by solubility concerns. Where reference is made to alkyl or R, R' etc. the alkyl moiety should have 1–12 carbon atoms. Suitable aryl moieties include phenyl and naphthyl as exemplary moieties. Particularly preferred species include chloro and alkoxy. As set forth therein, electron donating groups, such as a methoxy group, enhance anion decomposition process, whereas electron-withdrawing groups, such as chlorine, may retard the same decomposition reaction. Surprisingly, the influence of substituents on the aryl ring may be quite opposite that on the adamantyl or other steric stabilizing group. In the alternative, Y may be an organic linker group, of 1–20 carbon atoms, providing a covalent linkage between the dioxetane of the invention and a biological moiety to be studied, as described in U.S. Pat. No. 5,800,999, incorporated herein by reference. In this embodiment, the dioxetane or its precursor serves as a direct label, rather than indirect, and may be effectively triggered by agents other than enzymes, such as pH, heat, etc. In these embodiments, the identity of X (described below) may be other than an enzyme-label group.

In another alternative, Y may be OX'. As discussed herein below, X is the triggering group, that is, the group whose activation or removal leads to decomposition of the dioxetane through cleavage of the C—C and O—O bonds of the ring. The OX group meta with respect to the point of attachment of the benzothiazole group to the dioxetane is the primary triggering agent. Additional triggering, or reduced triggering, may be effected by setting Y equal to OX'. In the event this selection is made, X' is selected, independently, from the same set of variables that may characterize X.

In classic embodiments, X is an enzyme-labile group. Although preferred groups include phosphate moieties and galactoside moieties, virtually any enzyme-cleavable group, which, upon cleavage, leaves the oxyanion, is suitable for use in this invention. A large variety of enzyme-cleavable groups are set forth in U.S. Pat. No. 5,605,795, which is incorporated herein by reference. In general, in addition to the phosphate esters, moiety X may be any of the moieties identified for group Z in U.S. Pat. No. 5,605,795, incorporated herein by reference, including substrates for esterases, decarboxylases, phospholipases, α- or β-xylosidase, fucosidases, glucosidases, and thioglucosidases, galactosidases, mannosidases, fructofuranosidases, glucosiduronases, trypsin, etc. Additionally, moiety OX can be replaced by any of a wide variety of peptides cleavable by proteolytic enzymes, as set forth in U.S. Pat. No. 5,591,591, incorporated herein by reference.

As previously noted, there are situations where non-enzymatic chemical triggering, as opposed to enzymatic triggering, may be preferable. In these instances, X is preferably H, trialkylsilyl, etc. Various chemical triggering, and identities for X, are set forth, e.g., in U.S. Pat. 5,652,345, also incorporated herein by reference.

Figure 5:
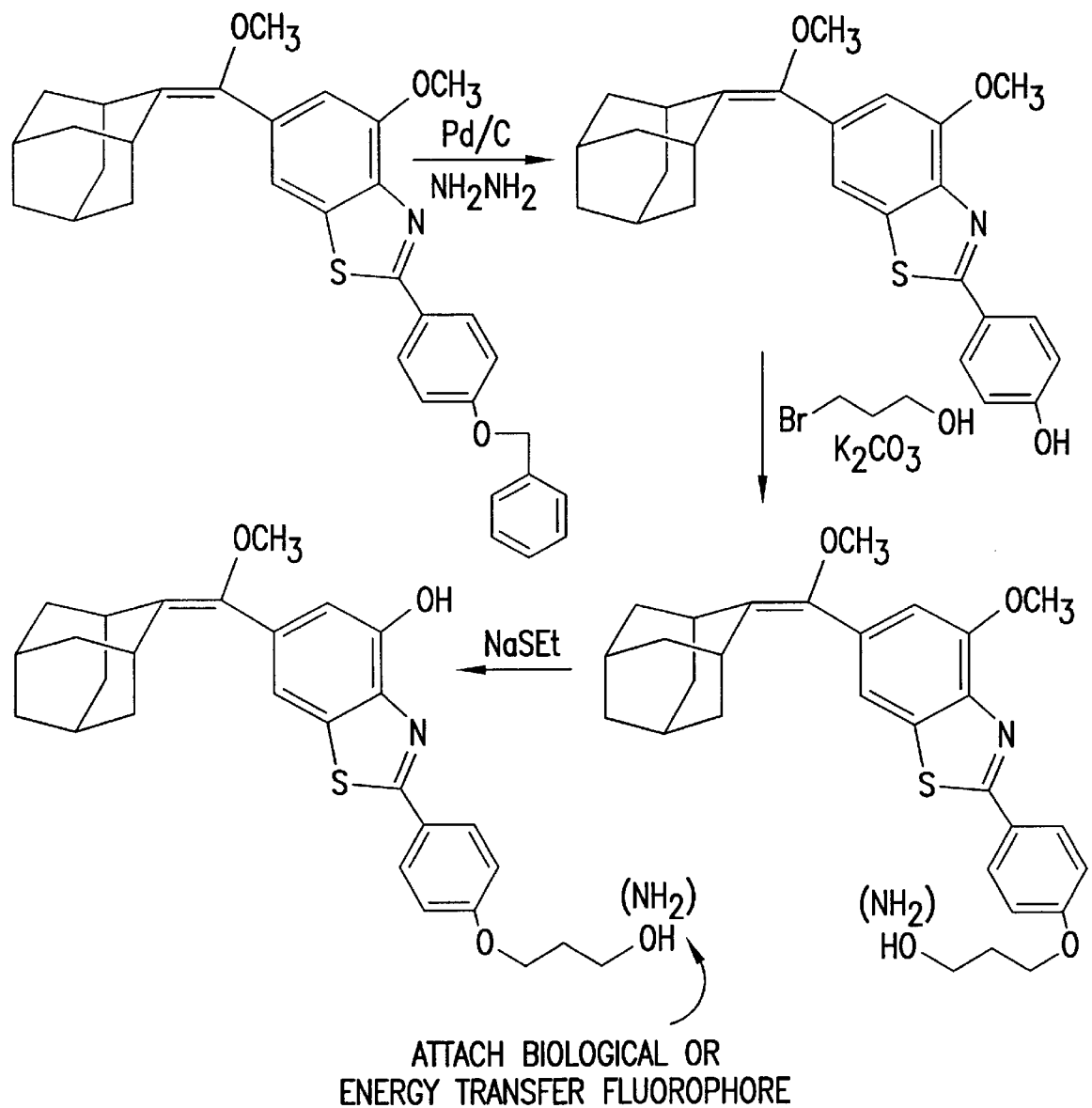
FIGS. 5 and 6 illustrate the synthesis and structure of a red-emitting dioxetane system using energy transfer.
Figure 6:
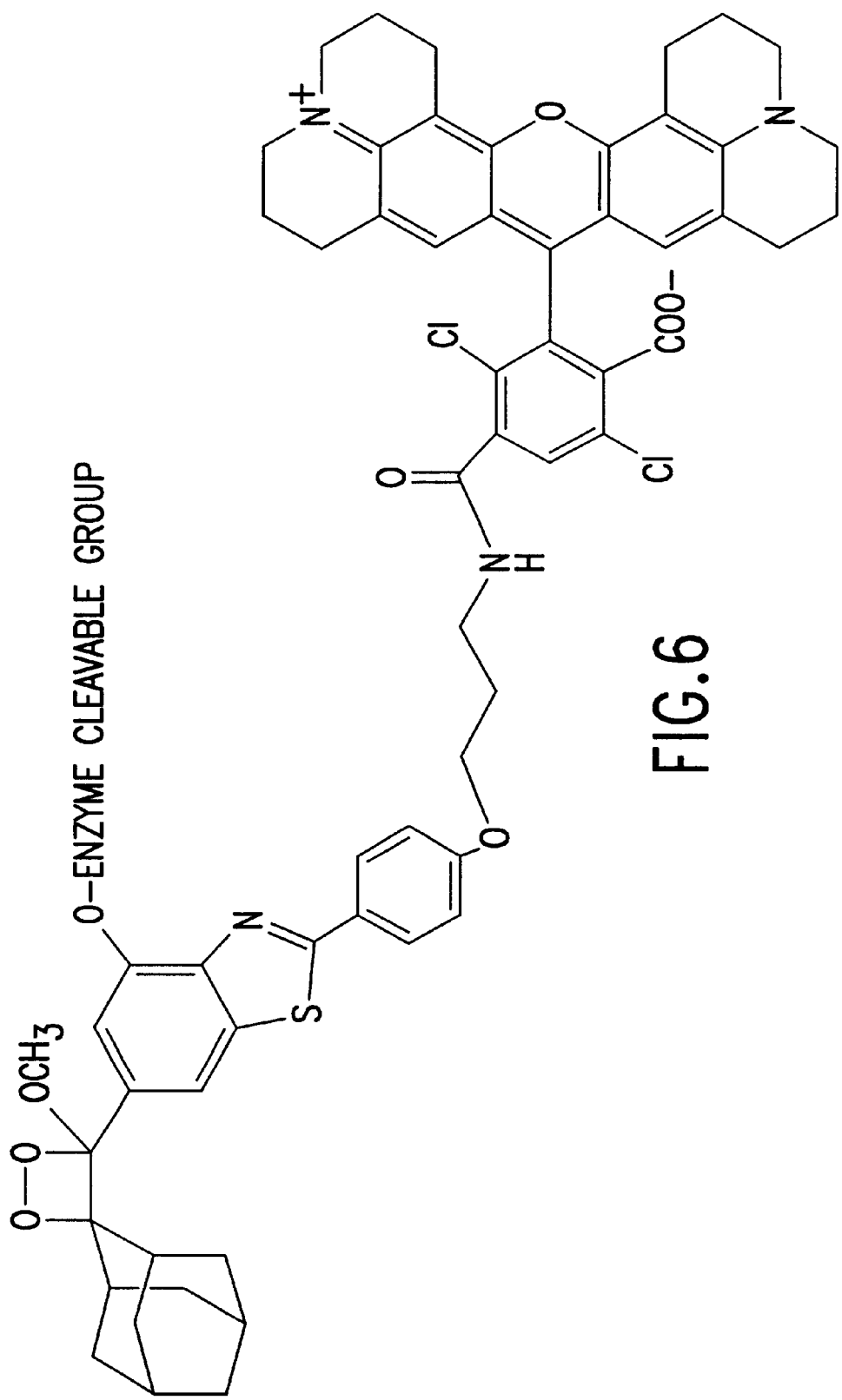

In monitoring, and measuring (quantifying) chemiluminescence, a wide variety of apparatus have been developed. Among the most sensitive, and particularly suited to high throughput screening applications and the like, are CCD cameras. Typical luminescent emission from dioxetanes is in the blue wavelengths of the visible spectrum. CCD cameras have difficulty "seeing", that is, registering, blue emission. Typically, only the "edge" of the longer wavelengths of the blue emission are observed by the camera. By employing a fused benzothiazole resonating moiety on the dioxetane, the light is green-shifted, that is, the emission is shifted toward the green end of the visible spectrum. Prior art dioxetanes are typically used with enhancement agents, which are configured so as to sequester the dioxetane in hydrophobic regions, to avoid the chemiluminescent quenching that can be observed in the presence of water. These enhancement molecules are preferably onium quaternary polymers, including phosphonium, sulfonium and ammonium polymers. Representative polymers, and their effects, are set forth in U.S. Pat. No. 5,330,900, which is incorporated herein by reference. These polymers may be used alone, or together with a surfactant additive, to further improve the enhancement value, as disclosed in U.S. Pat. No. 5,547,836, also incorporated herein by reference. Because of the green shifting of the dioxetane emission, and the enhanced hydrophobicity of the dioxetanes due to the presence of the fused benzothiazole, less enhancement agents, and if necessary, additives need be employed. As previously noted, moiety Y of the dioxetane can be used in a variety of functions. One function is as a linking arm. In addition to being a linker to a biological moiety of interest, Y may be an organic linking group (typically alkyl or alkoxy) attached to an energy transfer fluorophore, a florescent moiety which absorbs the energy emission of the dioxetane on decomposition, and fluoroesces in response thereto. Energy transfer fluoresensce is well established, and illustrated in FIG. 5 and FIG. 6.

Figure 2B:
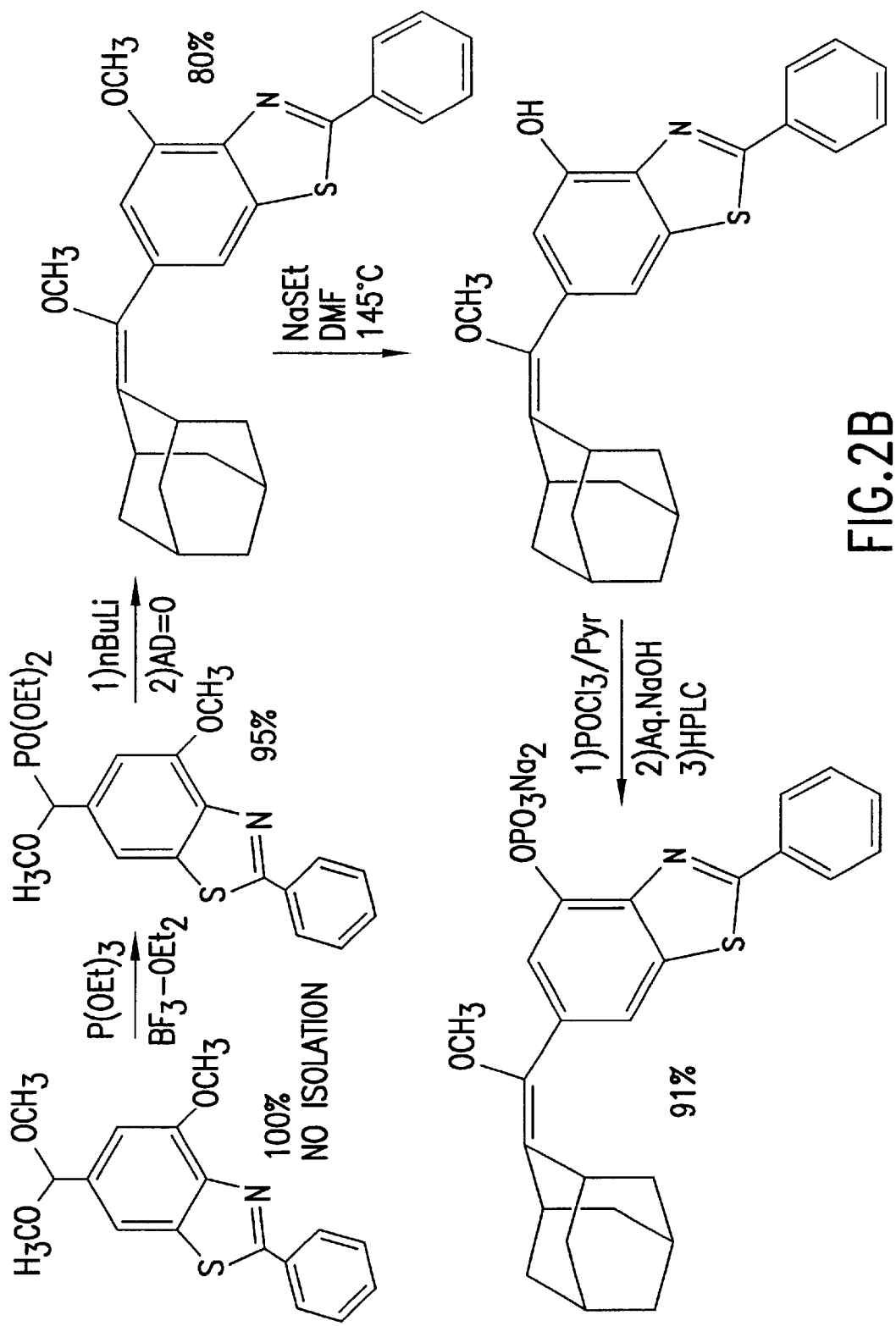
FIGS. 2 and 3 show the synthesis of the dioxetane of formula I of the invention.
Figure 3:
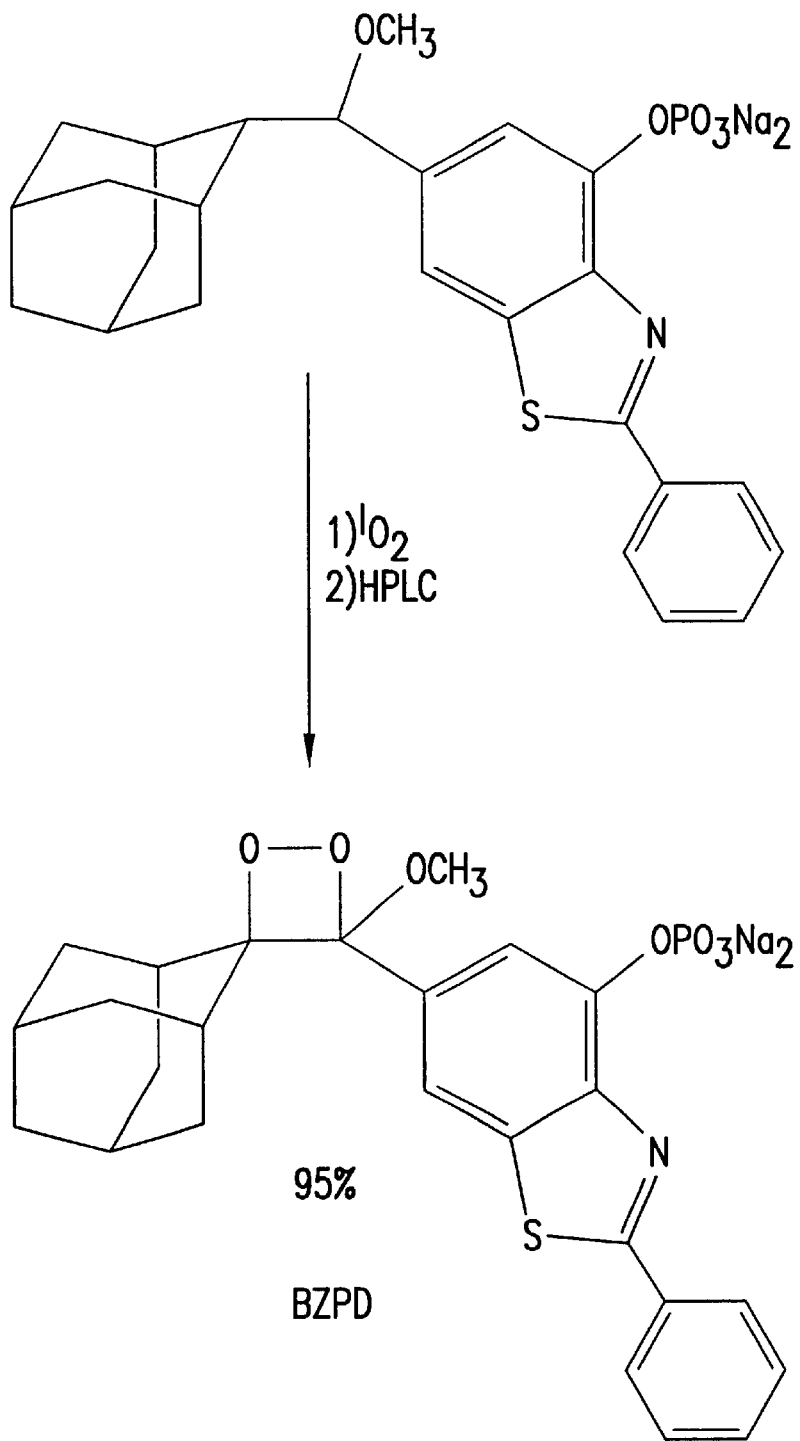
Figure 4:
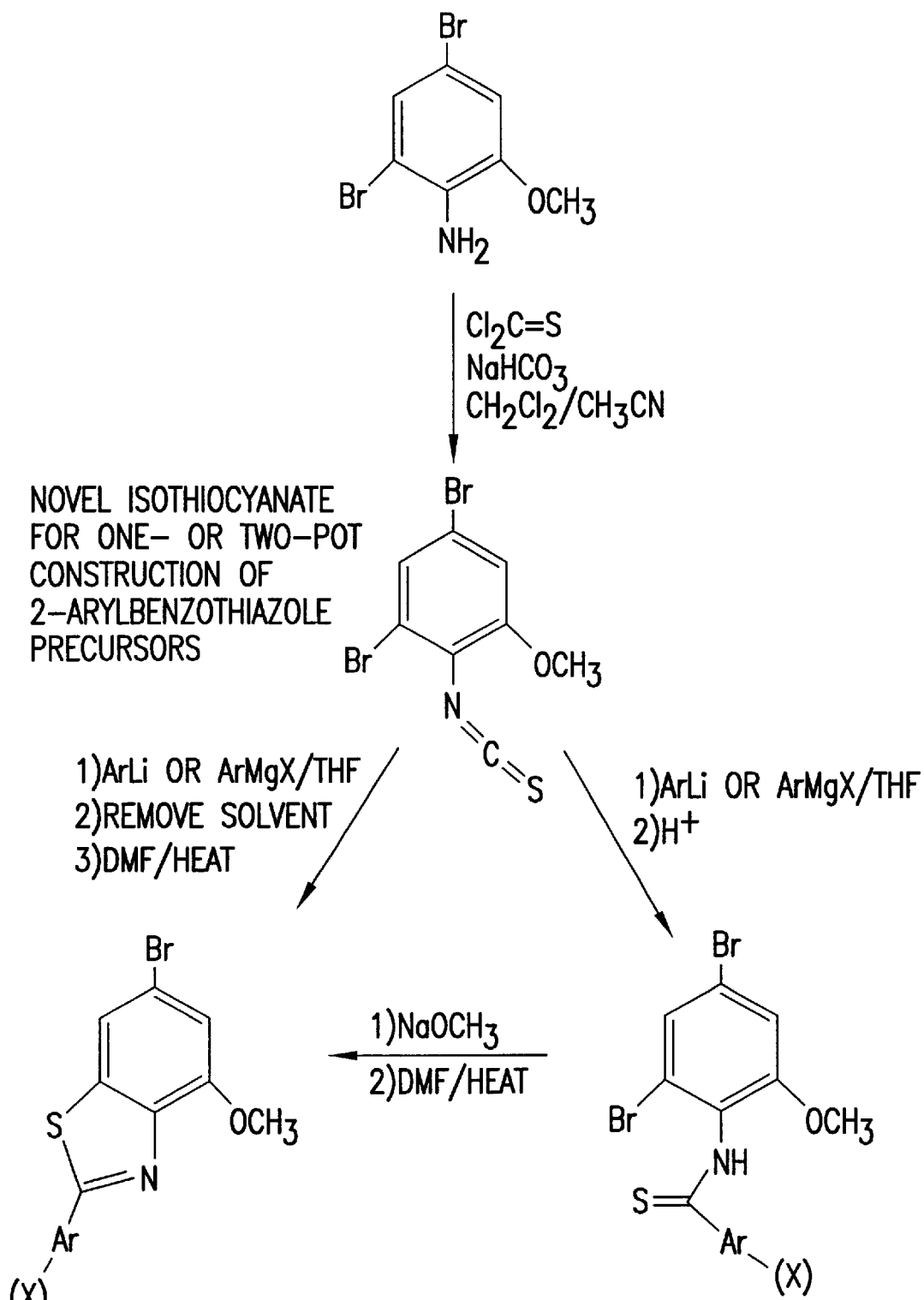
FIG. 4 illustrates a synthesis of an intermediate for the dioxetanes of formula I of the invention.

Referring more particularly to the figures of the application, FIG. 1 presents the chemical structure of a preferred embodiment of the invention, benzothiazole dioxetane phosphate. This molecule is referred to, herein, as BZPD. The synthesis of this dioxetane is illustrated in FIGS. 2 and 3, and the necessary reactions for synthesis are set forth below. Although conventional starting materials may be used to synthesize the dioxetancs of the claimed invention, novel isothiocyanate are set forth as an aspect of the invention, and illustrated in FIG. 4.

Figure 7:
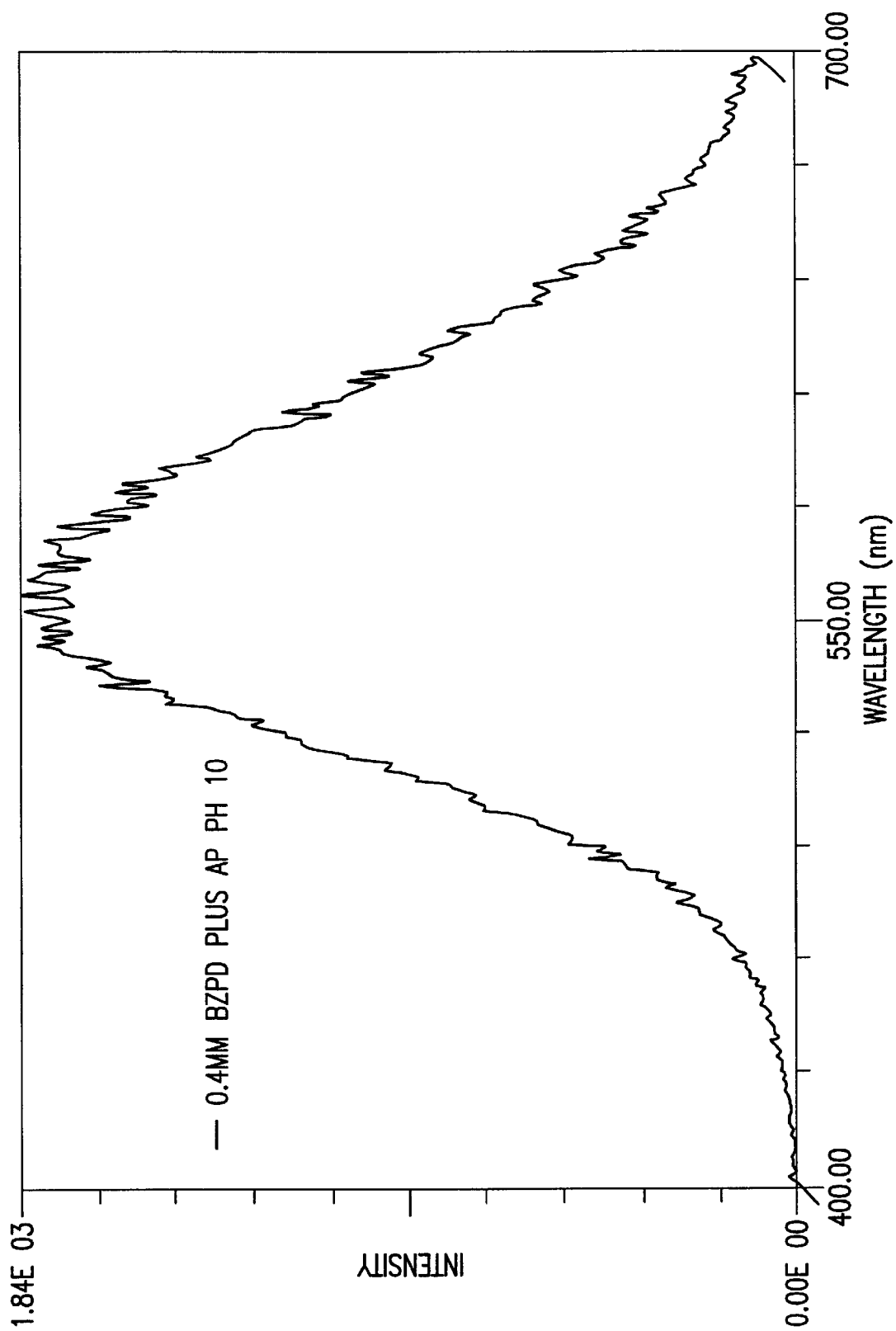
FIGS. 7 and 8 reflect the emission spectrum of the dioxetane of this invention.
Figure 8:
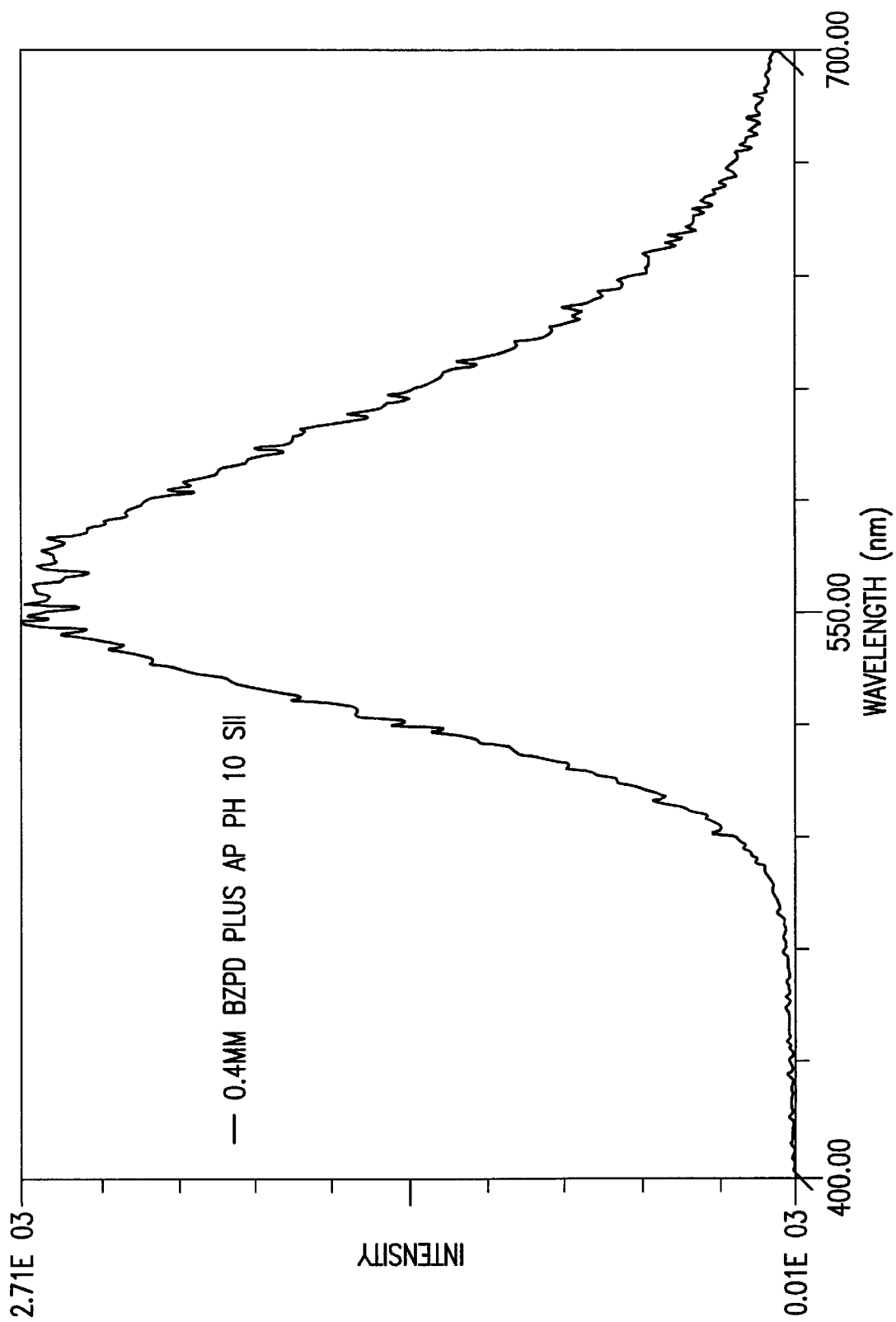
Figure 9B:
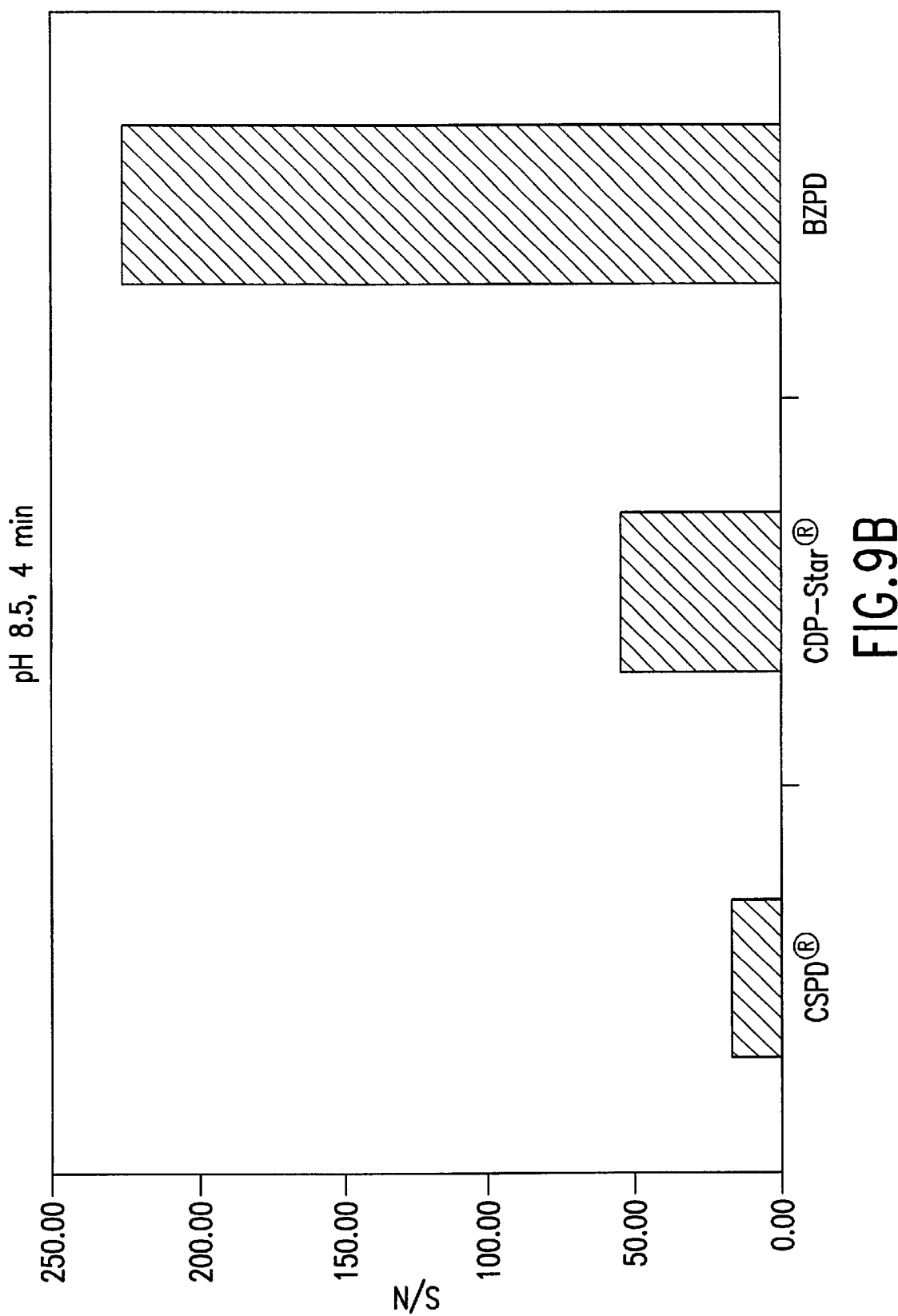

FIG. 7 illustrates the "green shifting" of the wavelength emission of BZPD, showing a peak wavelength above 550 nm, in the absence of any enhancement agent. As shown in FIG. 8, in the presence of an enhancement agent (Sapphire-II™), long wavelength intensity is further enhanced. The relative chemiluminescent performance of BZPD is compared with other commercially successful dioxetanes in FIGS. 9–12. Thus, the relatively "quick" or short $T_{1/2}$ of BZPD is illustrated in FIG. 9-A, compared with CSPD® (phenyl dioxetane bearing a chlorine substituent on the adamantyl group) and CDP-Star® (further bearing a chlorine on the phenyl moiety). The inventive dioxetanes also have an excellent S/N performance, as shown in FIG. 9-B. S/N values are of importance, because if the noise background is too high (a low S/N), no matter how rapidly the peak intensity is developed, the assay is relatively insensitive.

Figure 10B:
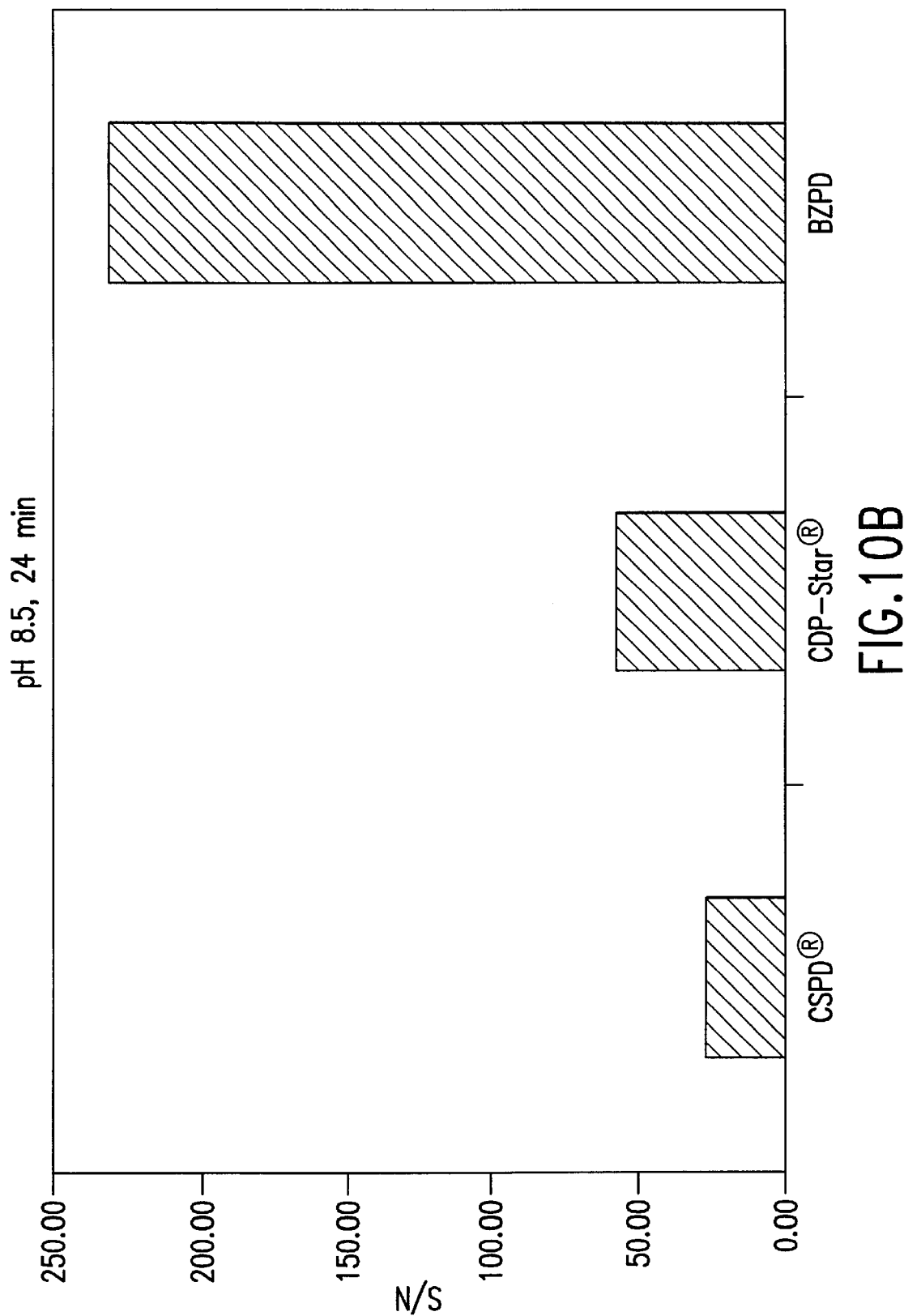
FIGS. 10A and B illustrate the speed of chemiluminescent kinetics and sensitivity of the inventive dioxetanes as opposed to commercial prior art dioxetanes.

FIGS. 10-A and 10-B reflect similar performance after 24 minutes, showing the continued heightened sensitivity and emission profile of BZPD.

Figure 11A:
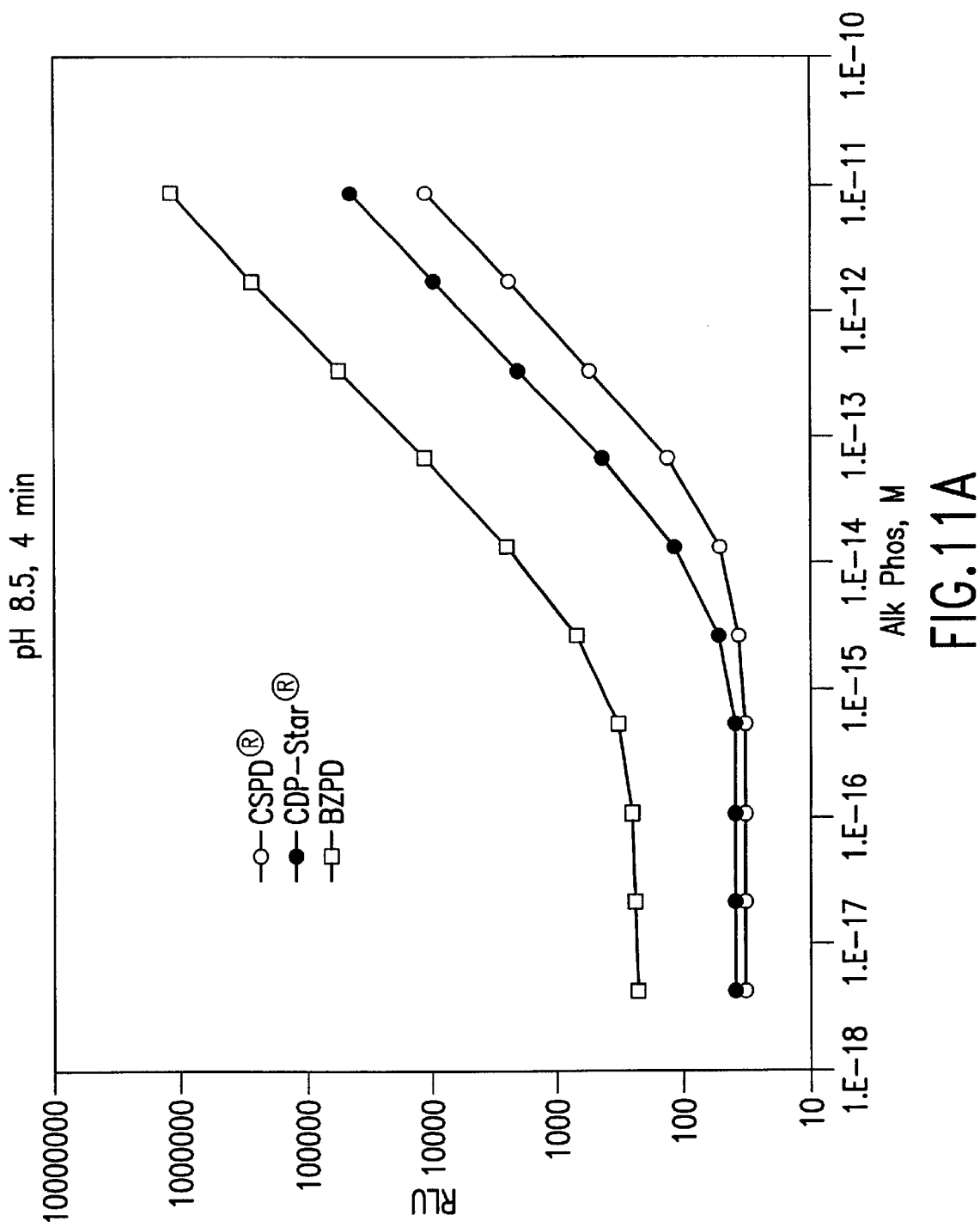
FIGS. 11A and B illustrate the speed of chemiluminescent kinetics and sensitivity of the inventive dioxetanes as opposed to commercial prior art dioxetanes.
Figure 11B:
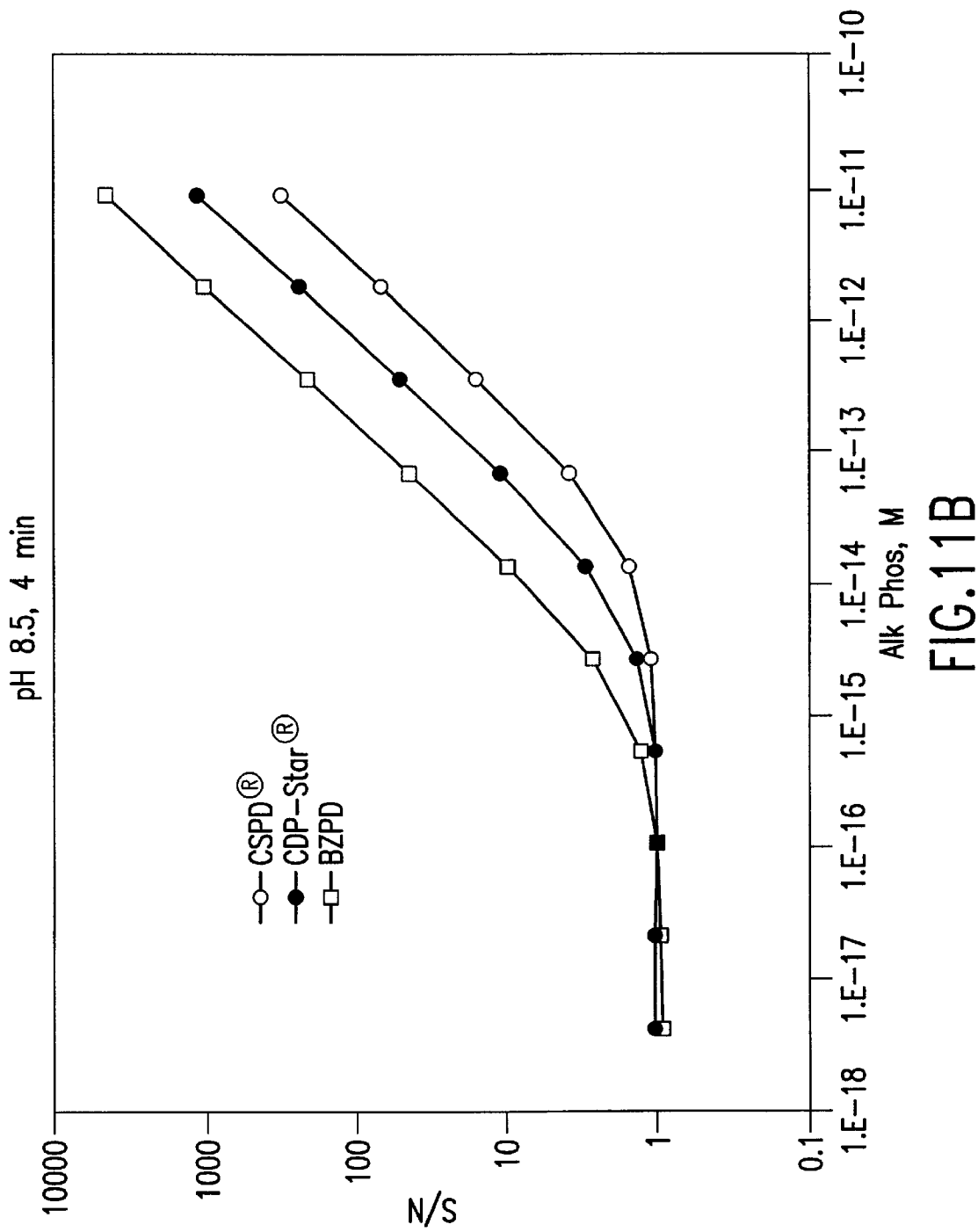
Figure 12A:
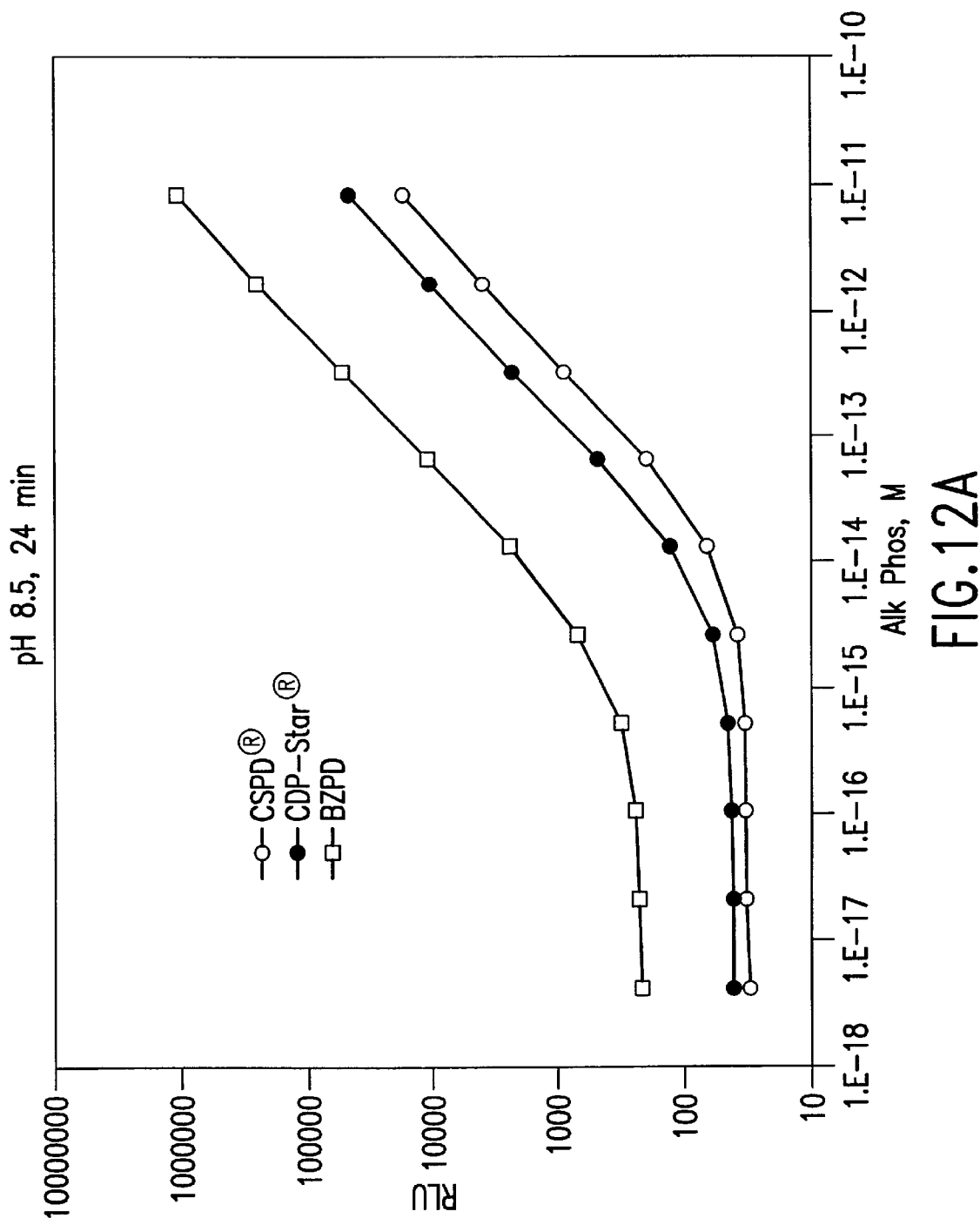
FIGS. 12A and B illustrate the speed of chemiluminescent kinetics and sensitivity of the inventive dioxetanes as opposed to commercial prior art dioxetanes.
Figure 12B:
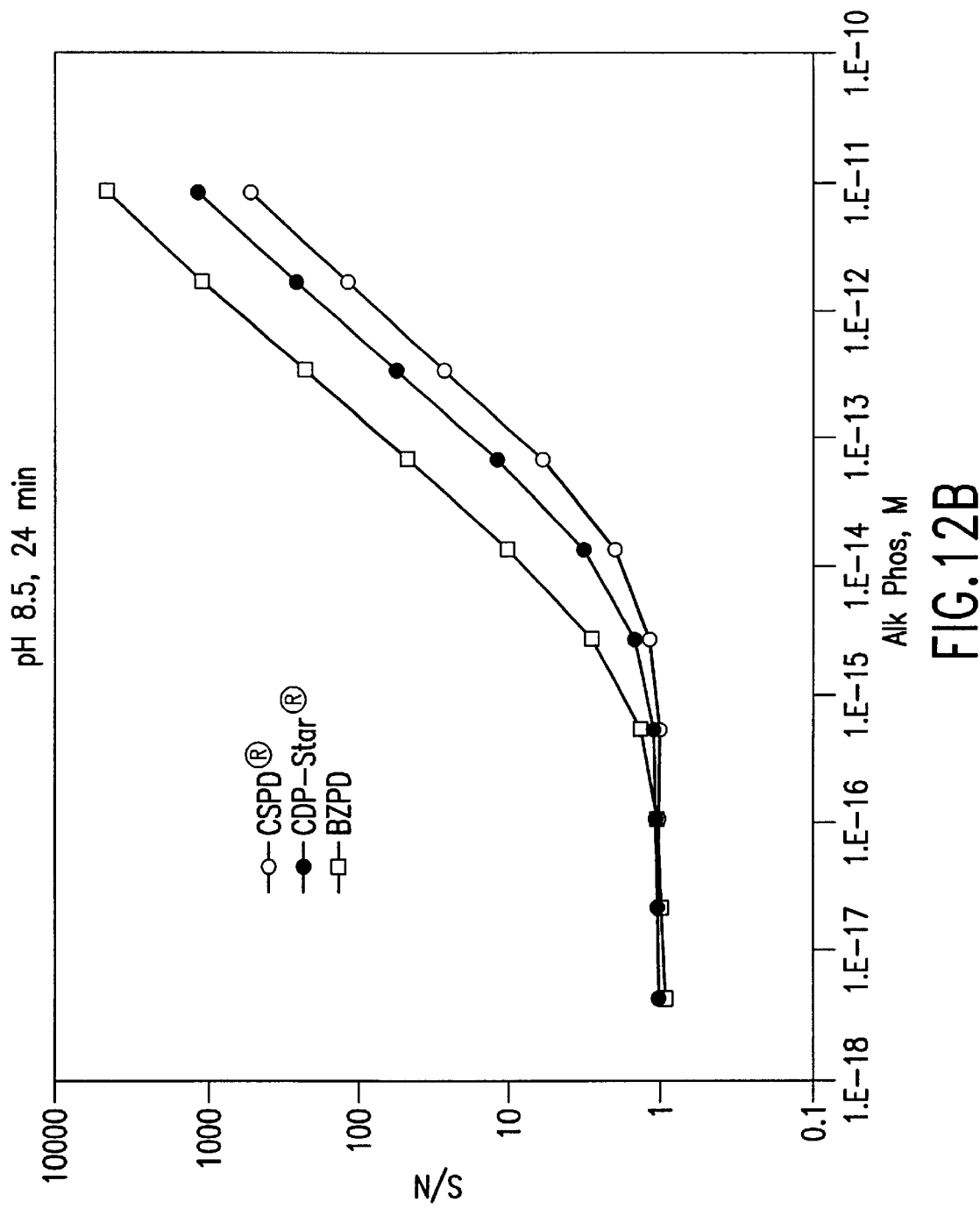

Sensitivity, is an essential characteristic of dioxetane detection agents. In FIGS. 11-A and 12-A, sensitivity after four minutes and 24 minutes, respectively, at various concentrations of alkaline phosphatase, for BZPD is measured. As clearly set forth, BZPD offers superior detection sensitivities (greater signal) even at very low concentrations of enzyme ($10^{-17}$ moles or less). As shown in FIGS. 11-B and 12-B, the S/N ratio of BZPD is comparable to previously developed dioxetanes, such that the heightened sensitivity can be used to detect very small amounts of material.

Direct synthesis of BZPD is described below.

The above dioxetanes may be synthesized by way of the fused benzothiazole aldehyde, or toluenene derivative using permangante oxidation. Esters of this acid may be used to prepare dioxetane precursors for the above compounds according to methodology described in U.S. Pat. No. 5,731,445 which is incorporated herein by reference.

Synthesis of Benzothiazole Dioxetanes Substrates

The following example is a representative synthesis of benzothiazole dioxetane substrates and their precursors, and should not limit the scope of the claims. 4,6-dibromo-o-anisidine was obtained according to the literature: Fuchs, Monatshefte fur Chemie, 36, 130, 1915. A Varian Unity 300 NMR Spectrometer was used. All NMR data is proton($^1$H) NMR

EXAMPLE 1

2-Benzamido-3,5-dibromoanisole 4,5-dibromo-o-anisidine (1 1.3 g; 40.2 mmol), was dissolved in 75 ml dichloromethane and 6.7 ml pyridine. The mixture was stirred at room temperature, under argon. Benzoyl chloride (4.8 ml; 1.03 equivalents), was added dropwise by syringe. The mixture was stirred for 8 hours to obtain an orange-brown suspension. The reaction mixture was then concentrated to one-third volume on the rotary evaporator. The thick slurry was filtered on a Buchner funnel, washing the flask and solid with 50:50 dichloromethane/hexanes. The resulting white solid was then washed liberally with water to remove any pyridine hydrochloride. The solid product was dried in vacuo to obtain 13.56 grams of the above-titled product. The biphasic filtrate was washed with water in a funnel, separating the organic layer which was then rotary evaporated to yield a purple brown solid. Trituration with 50:50 dichloromethane/ hexanes, and recrystallization from minimal ethyl acetate gave a second crop, weighing 1.43 grams.

NMR(300 MHz/DMSO-d6);δ 3.81(s, 3H), 7.36(1H), 7.44–7.71(m, 4H), 7.88–8.11(m, 2H) 9.88(s, 1H). IR(CH$_2$Cl$_2$/cm$^{-1}$): 3420, 2980, 2940, 1691, 1585, 1487, 1400, 1041, 875, 8370.

EXAMPLE 2

N-(2,4-dibromo-6-methoxy)phenylthiobenzamide

The product of the preceding example (14.4 g; 37.4 mmol), was dissolved in 35 ml dry pyridine with slight warming. Phosphorous pentasulfide (11 g; 49.5 mmol), was added in portions under argon. A thick, light yellow complex formed exothermically. This mixture was stirred for 2 hours in an oil bath at 90° C. to give a thinner, darker yellow suspension. The mixture was then refluxed for 15 minutes, and cooled to room temperature. The mixture was treated with 125 ml ethyl acetate to precipitate a gum. Water, 1 ml, was added with swirling to agglomerate the gum prior to decantation of the supernate. The gum was then triturated with 2×25 ml ethyl acetate. The combined organics were rotary evaporated to yield an orange oil which contained pyridine. A 7% solution of sodium hydroxide in water was added to the oil with vigorous stirring for 20 minutes. The solution was filtered to remove insolubles rinsing with minimal hydroxide solution. The filtrate was then acidified to pH 1 with 3M HCl, to precipitate a flocky, light yellow solid, which was dissolved in the minimal quantity of dichloromethane. The organic layer was separated and rotary evaporated to yield 12.6 g of the above-titled product as a lemon-yellow solid. Analytical samples could be obtained by recrystallization from ethanol to yield a one-spot material on TLC (Kieselgel 60-dichloromethane; Rf=0.56).

NMR(300 MHz/DMSO-d6):δ 3.81(s, 3H), 7.40–7.59(m, 6H), 7.90–7.93(m, 2H), 11.36(s, 1H). IR(CHCl$_3$/cm$^{-1}$): 3380, 2990, 1584, 1490, 1400, 1345, 1040, 878, 838, 695.

EXAMPLE 3

2-Phenyl-4-methoxy-6-bromobenzothiazole 12.6 grams of the thioamide from the preceding example (31.4 mmol) was warned in 30 ml of methanol. The suspension was swirled during the addition of 7.35 ml of 4.3 M sodium methoxide in methanol (31.6 mmol). During the addition the solid dissolved and the yellow color faded to light amber. Rotary evaporation of the solvent and pumping in vacuo gave an amber, glassy solid which coated the glass. This thioamide salt was kept under argon during the addition of 20 ml of N-methylpyrrolidone. The flask was capped with a septum and connected to a bubbler as it was placed in an oil bath at 110–120° C. Upon stirring for 30 minutes, a solid developed as the color became green-brown. The flask was then cooled toward room temperature before 100 ml of water was added to produce an off-white solid. The mixture was filtered and the solid washed liberally with water. After drying in vacuo, the solid was recrystallized from 50:50 ethyl acetate:hexanes to yield 7.05 g of white, hair-like needles. TLC showed the blue fluorescent product spot at Rf=0.47, while a trace UV absorbing impurity was present at a higher RF (Kieselgel 60-dichloromethane). The impurity could be removed by silica gel chromatography to obtain an analytical sample. NMR and IR data were consistent with the structure of the above-titled product.

NMR(300 MHz/CDCl$_3$):δ 4.10(s, 3H), 7.07(d, 1H), 7.49–7.52(m, 3H), 7.66(d, 1H), 8.11–8.14(m, 2H). IR(CHCl$_3$/cm$^{-1}$): 3003, 2940, 1590, 1562, 1517, 1440, 1400, 1387, 1322, 1260, 1055, 978, 830, 690.

EXAMPLE 4

2-Phenyl-4-methoxy-6-formylbenzothiazole 3 grams of the chromatographed product from the preceding example (9.37 mmol), was dissolved in 70 ml of dry THF under argon. In another flask, 60 ml dry THF was cooled and stirred at −78° under argon. To this flask, 5.6 ml of 2.5 M n-Butyllithium (14.1 mmol) was added by syringe. The solution of bromobenzothiazole starting material was then added dropwise under argon from an addition funnel over 25 minutes. THF, 7 ml, was used to rinse the funnel at the conclusion of the addition. The red-brown solution was stilted for another 10 minutes at low temperature. Dry DMF, 1.8 ml, was then added dropwise by syringe. After 10 minutes the solution was slowly warmed to room temperature over 1 hour. The reaction was quenched by the rapid addition of 20 ml of 1 M aqueous ammonium chloride solution. The THF was removed on the rotovap, and the product was partitioned between ethyl acetate and the remaining water. The ethyl acetate layer was washed four times with water to remove any DMF. The organics were dried over sodium sulfate and the solvent removed to yield a semi-solid paste. This was triturated with 20 ml of 20% dichloromethane in hexanes to yield a dry solid after decantation and pumping in vacuo. The resulting peach-colored product weighed 1.81 g TLC showed essentially one spot at an Rf value of 0.62 (Kieselgel 60–10% ethyl acetate/hexanes). Spectral data for a similarly obtained product were identical, and consistent with that expected for the above-titled compound.

NMR(300 MHz/CDCl$_3$):δ 4.18(s, 3H), 7.48–7.56(m, 4H), 8.04(d, 1H), 8.17–8.20(m, 2H), 10.08(s, 1H). IR(CHCl$_3$/cm$^{-1}$): 3010, 2840, 2740, 1695, 1595, 1572, 1480, 1470, 1395, 1290, 1270, 1145, 1057, 983, 850, 690.

EXAMPLE 5

2-Phenyl-4-metboxy-6-formylbenzothiazole dimethyl acetal

Under argon, 1.8 grams of the aldehyde from the previous example (6.7 mmol) was treated with 11 ml dichloromethane, 0.9 ml of trimethylorthoformate, and 0.7 ml of anhydrous methanol. The suspension was stirred as 105 mg of toluenesulfonic acid monohydrate was added all at once. The flask was closed with a septum after purging it with argon. The solid soon dissolved to give a yellow-orange solution. Stirring was continued overnight at room temperature. The reaction mixture was neutralized with excess triethylamine (0.15 ml) using a syringe. The mixture was stripped of all volatiles, dissolved in minimal dichloromethane, and plug-chromatographed on a 2 cm×1.5 inch column of Alumina. The eluant was rotary evaporated and pumped to an oil which slowly solidified. A sample was taken for immediate IR analysis, which showed the absence of any carbonyl absorption. This indicated that acetal formation was complete, and the crude product was used immediately for the next reaction. IR(CH$_2$Cl$_2$/cm$^{-1}$): 2940, 2840, 1602, 1580, 1468, 1410, 1355, 1198, 1155, 1060, 996, 837.

EXAMPLE 6

Diethyl-1-methoxy-1-(2-phenyl-4-methoxybenzothiazol-6-yl)methanephosphonate

The crude product obtained in the previous step was dissolved in 11 ml of sieve-dried dichloromethane and 1.5 ml of triethylphosphite under argon. The flask was sealed with a septum, and the stirred solution was cooled to −78° C. in a dry ice/acetone bath. The pressure was equilibrated at this temperature with an argon balloon. The mixture, which became a suspension, was then treated dropwise with 1.0 ml of borontrifluoride etherate. The suspended solid dissolved as the contents were slowly warmed to about −20° C. The solution was stored in the refrigerator for one hour, and then slowly warmed to room temperature for an overnight stirring period. In the morning, 0.7 grams of solid sodium bicarbonate was added, followed by 15 ml of saturated, aqueous sodium bicarbonate solution. The biphase was stirred vigorously to expel carbon dioxide. Water was added as necessary over 3 hours to dissolve any inorganics. The dichloromethane layer was separated, and the aqueous layer was back-extracted with 15 ml of the same solvent. The combined organics were subjected to TLC to show a single, UV/blue fluorescent spot at approximately Rf 0.15, tailing back to the origin (Kieselgel 60-ethyl acetate). The solution was evaporated and vacuum pumped at 40° C. The viscous yellow oil was then dissolved in a minimal amount of 50/50 dichloromethane/ethyl acetate and passed over a very short plug of silica gel. The eluant was stripped and chased several times with a mixture of dichloromethane/hexanes. The oily product weighed 2.7 grams. NMR and IR spectroscopy showed a substantially pure product, but the presence of moisture was indicated.

NMR(300 MHz/CDCl$_3$):δ 1.21–1.36(m, 6H), 3.46(s, 3H), 3.93–4.21(m, 7H), 4.59–4.64(d, 1H), 7.07(s, 1H), 7.47–7.52 (m, 3H), 7.57(s, 1H), 8.11–8.14(m, 2H). IR(CH$_2$Cl$_2$/cm$^{-1}$): 3660 & 3460(H$_2$O), 2980, 2935, 2860, 1597, 1570, 1510, 1480, 1460, 1445, 1408, 1342, 1245–1285(br), 1100, 1040 (br), 965(br), 865, 840, 610.

EXAMPLE 7

6-(Methoxytricyclo[3.3.1.1$^{3,7}$]dec-2-ylidenemethyl)-2-phenyl-4-methoxybenzothiazole 2.7 grams of the pumped phosphonate ester from the previous step (6.4 mmol), was dissolved in 25 ml of dry THF under argon. The solution was cooled to −78° C. with stirring in a flask outfitted with a septum and an argon balloon. The solution was treated dropwise with enough 2.5 M n-BuLi in hexanes to achieve a just permanent, red-purple color. In this process, all moisture and protic impurities have been titrated. Subsequently 2.7 ml of the same n-BuLi solution (6.75 mmol) were added dropwise to yield a deep burgundy solution. After 10 minutes stirring at low temperature, 2-adamantanone (0.95 grams, 6.33 mmol) was added as a solid under strong argon flow to exclude moisture. The solid dissolved over 10 minutes. The solution was then allowed to warm slowly to room temperature. A reflux condenser was attached while maintaining an argon atmosphere. The mixture was refluxed for 1.5 hours to obtain a light orange solution. THF was then stripped on the rotary evaporator taking care to avoid foaming. The product was partitioned between 25 ml ethyl acetate and 50 ml 1:1 saturated sodium bicarbonate/water. The organic layer was then washed with 25 ml of water. The organic layer was dried over sodium sulfate and stripped to yield a light yellow gum.

The gum was plug-chromatographed on a short column of silica gel, eluting with dichloromethane to remove trace polar contaminants. The appropriate fractions were pumped and chased with dichloromethane-hexanes. The pumped product, weighing 2.14 grams, became a semi-solid upon storage in the freezer. IR spectroscopy revealed a small 2-adamantanone carbonyl band, indicating minor contamination which would be eliminated in the next step.

IR(CH$_2$Cl$_2$/cm$^{-1}$): 2920, 2850, 1597, 1567, 1450, 1402, 1330, 1320, 1310, 1252, 1165, 1100, 1057, 978, 865, 640, 620. Trace AD=O at 1720 and 1710.

EXAMPLE 8

6-(Methoxytricyclo[3.3.1.1$^{3,7}$]dec-2-ylidenemethyl)-2-phenyl-4-hydroxybenzothiazole A sodium ethanethiolate solution in DMF was made from 60% sodium hydride and ethanethiol: 240 mg of 60% sodium hydride (6 mmol) was washed three times with hexanes under an argon atmosphere, removing the mineral oil. DMF, 11 ml, was added. The resulting suspension was cooled to 0° C. with stirring for the dropwise addition of ethanethiol (0.45 ml, 6 mmol). After hydrogen evolution ceased, the solution was warmed to room temperature, and delivered by pipett to 1.64 grams of methoxy[2-phenyl-4-methoxy(benzothiazole-6-yl)methylidene adamantane, in a separate flask (3.9 mmol) under argon. The resulting solution was stirred in an oil bath at 130° C. After one hour the solution was deep orange, and contained suspended solid. The reaction mixture was cooled and partitioned between 50 ml each of 1 M ammonium chloride and 75% ethyl acetate/hexanes. The organic layer was washed 3 times with 25 ml of water. The combined aqueous layers were back-extracted with the same solvent mixture, which was then washed several times with water. The combined organics were dried over sodium sulfate. TLC (Kieselgel 60-dichloromethane) showed product at Rf=0.23, but also starting material at Rf=0.39. Column chromatography (silica gel: 50% dichloromethane-hexanes to pure dichloromethane) allowed one pure fraction of the lower Rf product to be isolated. Repeat chromatography of the mixed fractions allowed additional product to be isolated. After stripping the solvents, a total of 245 mg of the above-entitled product was obtained.

NMR(300 MHz/CD$_2$Cl$_2$):δ 1.74–2.07(m, 14H), 2.71(s, 1H), 3.26 (s, 1H), 3.32(s, 3H), 6.76(s, 1H), 6.94(d, 1H), 7.38(d, 1H), 7.44–759(m, 3H), 7.99–8.16(m, 2H). IR(CH$_2$Cl$_2$/cm$^{-1}$): 3520, 2910, 2850, 1612, 1575, 1480, 1445, 1302, 1284, 1175, 1080, 980, 860.

EXAMPLE 9

Disodium 6-(methoxytricyclo[3.3.1.1$^{3,7}$]dec-2-ylidenemethyl)-2-phenylbenzothiazolyl-4-phosphate Molecular sieve-dried pyridine, 4.0 ml, was placed in a flask under argon. The flask was outfitted with a magnetic stir bar and placed in an ice bath. Distilled phosphorus oxychloride, 0.112 ml (1.2 mmol), was added dropwise by syringe. In another flask, 245 mg of the hydroxybenzothiazole derivative from the previous example was dissolved in 15 ml of anhydrous THF under argon. The THF solution was then added slowly and dropwise to the stirred solution of phosphorylating agent. During the addition, a precipitate developed. At the end of the addition, the flask and syringe were rinsed with 2 ml of THF which was also added slowly to the reaction flask. The reaction mixture was then warmed to room temperature and stirred for three hours. A cotton-tipped needle on a 20 ml syringe was used to draw up the supernate, leaving the pyridine hydrochloride behind. This supernate was added dropwise to a solution of 15 ml 0.5 M sodium hydroxide, which had been diluted to a volume of 75 ml with water, while being stirred at icc-bath temperature.

The slightly cloudy solution cleared upon warming to room temperature. The solution was carefully pumped to remove THF and the volume adjusted to 110 ml with 5.0 ml acetonitrile and water. This solution was injected in two portions onto a Polymer Laboratories 2 inch polystyrene reverse-phase HPLC column. A gradient of 5% to 10% acetonitrile was used to allow separation of the major peak absorbing at 270 nm. This gradient will require optimization for any specific equipment. The appropriate fractions were pooled and lyophilized to obtain 294 mg of a light yellow solid. Spectral data were in concert with the above-titled structure. An analytical HPLC chromatogram on a similar support, using an acetonitrile gradient against 0.1% aqueous sodium bicarbonate, showed a single product eluting at 13.2 minutes (approximately 50% acetonitrile).

NMR(300 MHz/$D_2O$):δ 1.38–2.02(m, 14H), 2.51(s, 1H), 3.00(s, 1H), 3.24(s, 3H), 7.26–7.53(m, 5H), 7.75–8.04(m, 2H).

EXAMPLE 10

Disodium 6-(4-methoxyspiro-[1,2-dioxetane-3,2'-tricyclo[$3.3.1.1^{3,7}$]decan]-4-yl)2-phenylbenzothiazolyl-4-phosphate 285 milligrams of the enol ether phosphate from the previous step was placed in a tube. The solid was wet down with 1.0 ml of methanol and then dissolved by adding 25 ml of dichloromethane. The solution was then treated with 0.5 ml of a solution of 5, 10, 15, 20-tetraphenyl-21 H, 23 H-porphine (2 mg/ml in $CHCl_3$). The contents of the tube were cooled to 0° C. while the solution was sparged with oxygen gas. After 5 minutes, while continuing to bubble oxygen through the solution, the tube was irradiated with light from a cooled, 400 watt sodium vapor lamp while maintaining the temperature at 5° C. A 5 mil thick piece of Kapton polyimide film, placed between the lamp and the tube filtered out unwanted UV radiation. The irradiation was continued for 17 minutes. Analytical HPLC [0.1% $NaHCO_3$ ($H_2O$)-acetonitrile gradient] showed that the conversion of the starting material, eluting at 13.2 minutes, to the 1,2-dioxetane, which eluted at 12.94 minutes, was substantially complete. The reaction mixture was stripped of solvents to give a red gum. Acetonitrile, 5 ml, and 0.05 M aqueous sodium hydroxide, 20 ml, were added with swirling and occasional cooling to dissolve the gum. DI water was then added to give a total volume of 70 ml. This solution was filtered through highly retentive filter paper, rinsing carefully with water in small portions, to give a filtrate volume of 110 ml. This solution was injected in two portions onto a Polymer Laboratories 1 inch polystyrene reverse-phase HPLC column. A gradient of 5% to 100% acetonitrile (against water) was used to allow separation of the major peak absorbing at 270 nm. This gradient will require optimization for any specific equipment. An analytical HPLC chromatogram of the combined product fractions on a similar support, using an acetonitrile gradient against 0.1% aqueous sodium bicarbonate, showed a single product eluting at 12.96 minutes (approximately 50% acetonitrile). The appropriate fractions were pooled and lyophillized to obtain 287 mg of a light yellow solid. The product 1,2-dioxetane produced green light at 558 nm when triggered with alkaline phosphatase in an aqueous buffer at pH 8.5.

UV: 213, 260.5, and 304 nm in 50/50 $CH_3CN/H_2O$

EXAMPLE 11

2-Methoxy-4,6-dibromophenylisothiocyanate 19.75 grams of 4,6-dibromo-o-anisidine (70 mmol) and 20 grams of solid bicarbonate were placed in a flask under argon. A large, heavy-duty magnetic stir bar was added, followed by 120 ml acetonitrile and 50 ml dichloromethane. The suspension was stirred at 0° C. as 6.0 ml of thiophosgene was added rapidly by syringe. A thick precipitate developed immediately. This was stirred vigorously as the contents of the flask were slowly warmed to room temperature. The carbon dioxide generated was led to a bubbler with a needle vent. The mixture thinned slightly as it warmed, and was more easily stirred. Vigorous stirring was continued for two hours. The suspension was then recooled to 0° C. The solid was filtered off on a Buchner funnel, rinsing the flask and transferring any remaining solid with 30 ml of cold acetonitrile. The filtrate was rotary evaporated to a solid containing areas of orange discoloration. This solid was triturated with hexanes, pumped dry, and transferred to the Buchner funnel containing the white, original filter cake. This solid was washed with 5×100 ml portions of a 0.5 M aqueous solution of $NaH_2PO_4$ in order to neutralize the inorganic bicarbonate present (carbon dioxide was released). The solid was broken up during each rinse. The white product was then washed liberally with water and dried in vacuo. The dry product weighed 21.8 grams. Analytical data obtained from a similarly synthesized product were in agreement with the above-titled structure.

NMR(300 MHz/$CDCl_3$):δ 3.92(s, 3H), 6.98(d, 1H), 7.31 (d, 1H). IR($CH_2Cl_2/cm^{-1}$): 3020, 2970, 2940, 2030(br), 1575, 1555, 1470, 1400, 1040, 935, 870, 840.

EXAMPLE 12

2-Phenyl-4-methoxy-6-bromobenzothiazole[One Pot Method]

15.5 grams of the isothiocyanate from the preceding example (48 mmol), was dissolved in 50 ml of dry THF under argon. The solution was cooled to 0° C. with stirring in an ice bath. A solution of phenlymagnesium bromide (Aldrich, 1.0 M in THF), 50 ml (50 mmol), was added by syringe in a thin stream. After stirring in the cold for 10 minutes, the solution was slowly warmed to room temperature. At this point a precipitate began to appear as a minor exotherm occurred. The light orange-brown suspension became thicker over 2 hours. The solvent was removed by rotary evaporation at 30° C. to obtain a moist, peach-colored solid coating the glass. This material was protected from air as 50 ml of sieve-dried DMF was added. The solid dissolved with a slight exotherm. The flask was placed in an oil bath at 125° C. Over 45 minutes, any residual THF was allowed to distill from the flask using a short path distillation head. The mixture darkened during this time, and a suspended solid was produced. Upon cooling to room temperature, the contents of the flask solidified. Aqueous 1 M HCl, 100 ml was added, breaking up the solid. Water, 100 ml, was added subsequently. The mixture was macerated to remove any coordinated magnesium ion. The mixture was then filtered and washed well with water. The moist solid was taken up in 2×250 ml warm ethyl acetate, separating the supernate from insoluble flock. The combined organics were dried over sodium sulfate and stripped to give 13.27 grams of a light brown solid. TLC showed a major blue fluorescent product spot at Rf=0.47, while a trace UV absorbing impurity was present at a higher Rf (Kieselgel 60-dichloromethane). A small, colored origin spot was removed by plug chromatography over silica gel (dichloromethane). Combining the appropriate fractions gave 12.29 grams of the product, essentially identical to that of Example 3, but still containing a trace amount of the higher Rf impurity. The reaction of this example may also be acidified and worked up after the phenyl magnesium bromide has reacted with the isothiocyanate to obtain the thioamide product of Example 2.

The following were also synthesized according to the general synthetic methodology described above. One of skill in the art may easily invoke minor modifications as necessary. Any other route to the benzothiazole system may be employed as well.

EXAMPLE 13

2-(p-benzyloxybenzamido)-3,5-dibromoanisole

NMR(300 MHz/DMSO-d6):δ 3.79(s, 3H), 5.21(2H), 7.1–7.14(d, 2H), 7.34–7.52(m, 7H), 7.93–7.96(d, 2H), 9.70 (s, 1H).

EXAMPLE 14

N-(2,4-dibromo-6-methoxy)-p-benzyloxyphenylthiobenzamide

NMR(300 MHz/DMSO-d6):δ 3.80(s, 3H), 5.22(2H), 7.08–7.11(d, 2H), 7.32–7.55(m, 7H), 7.95–7.98(d, 2H), 11.12(s, 1H).

EXAMPLE 15

2-(p-benzyloxy)phenyl-4-methoxy-6-bromobenzothiazole

NMR(300 MHz/DMSO-d6):δ 4.00(s, 3H), 5.21(2H), 7.17–7.22(m, 3H), 7.34–7.50(m, 5H), 7.93–8.01(m, 3H).

EXAMPLE 16

2-(p-benzyloxy)phenyl-4-methoxy-6-formylbenzothiazole

NMR(300 MHz/DMSO-d6):δ 4.05(s, 3H), 5.23(2H), 7.20–7.23(d, 2H), 7.33–7.50(m, 6H), 8.05–8.08(d, 2H), 8.31–8.32(d, 1H), 10.04(s, 1H).

EXAMPLE 17

2-(p-benzyloxyphenyl-4-methoxy-6-formylbenzothiazole dimethyl acetal IR(CHCl$_3$/cm$^-$$_1$): 3000, 2940, 2840, 1611, 1580, 1530, 1490, 1470, 1355, 1180, 1155, 1060, 1020, 980, 838, 700.

EXAMPLE 18 diethyl-1-methoxy-1-[2-(p-benzyloxy)phenyl-4-methoxybenzothiazol-6-yl]methanephosphonate NMR(300 MHz/CDCl$_3$):δ 1.19–1.37(m, 6H), 3.43(s, 3H), 3.86–4.18(m, 7H), 4.51–4.75(m, 1H), 5.12(s, 2H), 7.02–7.03(m, 2H), 7.30–7.52(m, 7H), 8.02–8.06(m, 2H).

EXAMPLE 19

6-(Methoxytricyclo[3.3.1.1$^{3,7}$]dec-2-ylidenemethyl)-2-(p-benzyloxy)phenyl-4-methoxybenzothiazole NMR(300 MHz/CDCl$_3$):δ 1.78–2.1(m, 14H), 2.74(s, 1H), 3.30(s, 1H), 3.35(s, 3H), 4.06(s, 3H), 5.12(s, 2H), 6.85–6.96 (m, 1H), 6.99–7.12(m, 2H), 7.29–7.50(m, 6H), 7.99–8.14 (m, 2H).

TABLE 1

Half-life of Dephosphorylated dioxetanes pH 10.

| Dioxetane | t½, sec |
|---|---|
| BZPD | 2.3 |
| CSPD ® | 57.6 |
| CDP-Star ® Plus Sapphire-II ™ | 96 |
| BZPD | 54.9 |
| CSPD ® | 228 |
| CDP-Star ® | 420 |

The 1,2-dioxetanes of this invention can be used in a method to detect a substance in a sample, wherein the substance is capable of removing X of the general formula. The sample with the 1,2-dioxetane of the invention is incubated, and then inspected for the generation of light. If light is detected, the presence of the substance which removes X is indicated, and the amount of light detected indicates the amount of the substance present in the sample. Typically, the substance is an enzyme, which is selected for X, and by removing X, causes the dioxetane to decompose. The enzyme may be complexed to a biological moiety of interest. The methods may be used in conjunction with the enhancement molecules, preferably the onium quaternary polymers, and additives, discussed above, and set forth in U.S. Pat. Nos. 5,330,900 and 5,547,836. In preferred embodiments, the light emitted by the decomposition of the 1,2-dioxetane of the invention is detected by a CCD camera.

These assays can be made possible by providing kits which include the 1,2-dioxetanes of the invention, either alone, or together with an enzyme or other substance which causes the dioxetane to decompose by removing X. The water soluble enhancers, and additives which improve the water soluble enhancers, can also be present in the kits.

What is claimed is:

1. A 1,2-dioxetane compound capable of producing light energy when decomposed, represented by the formula:

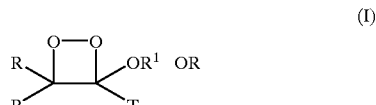

(I)

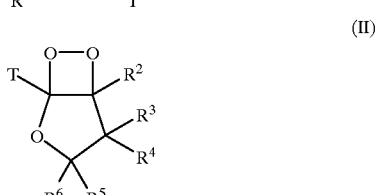

(II)

-continued wherein T is:

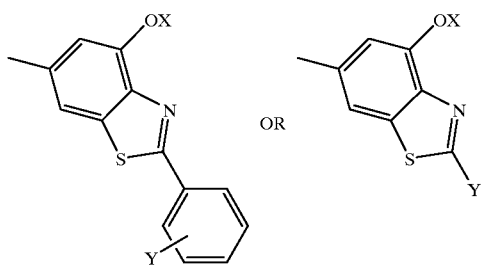

and wherein R may independently be any branched alkyl or cycloalkyl group which provides stabilization for the dioxetane or where both R groups together form a cycloalkyl or polycycloalkyl moiety spiro bound to the dioxetane ring, wherein each R group or the spiro bound moiety may be unsubstituted or substituted with one or more electron-withdrawing groups or electron donating groups, and wherein $R^1$ is an aryl group, or an alkyl group of 1–20 carbon atoms, which may be optionally substituted with 1 or more halogen atoms, and wherein Y may be H, or an electron donating or withdrawing group, or an organic linker group which may be attached to (1) an ancillary fluorophore, or (2) any biological moiety, and wherein X may be any protecting group which is removed by non-enzymatic chemical or enzymatic means, where $R^2$–$R^6$ are each independently H, alkyl of 1–20 carbon atoms, or an aryl group, where each of $R^2$–$R^6$ may be unsubstituted or substituted one or more with electron-donating groups or electron-withdrawing groups, wherein $R^3$ and $R^4$ may be joined as a spiro-fused cycloalkyl group.

2. The compound of claim 1, wherein X is a phosphate, both R groups together form a spiroadamantyl group, and $R^1$ is methyl, and Y is hydrogen.

3. The compound of claim 1, wherein at least one of an R group, $R^2$–$R^6$ and Y bear a substituent which improves the solubility of said dioxetane in an aqueous solution.

4. The compound of claim 2, wherein each substituent improving solubility is a carboxylic acid moiety, a sulfonic acid moiety or a phosphoric acid moiety.

5. The compound of claim 1, wherein at least one of $R^2$–$R^6$ is substituted with an electron-active group.

6. The compound of claim 1, wherein X is an enzyme removable group.

7. The compound of claim 1, wherein X is a moiety which is removed by a change in pH or heat.

8. The compound of claim 1, wherein Y is an alkyl or alkoxy moiety linked to a fluorophore in an energy transfer relationship with said dioxetane.

9. A kit for detecting a first substance in a sample, comprising the 1,2-dioxetane compound of claim 1.

10. The kit of claim 9, further comprising an enzyme which, in the presence of said dioxetane, causes said dioxetane to decompose.

11. The kit of claim 10, further comprising a water soluble enhancing substance which enhances a chemiluminescence emission detectable from the decomposition of said dioxetane.

12. The kit of claim 11, wherein said enhancing substance is a quaternary onium polymer.

13. The kit of claim 11, wherein said kit further comprises an enhancement additive which improves the enhancement of detected chemiluminescence emission effected by said enhancing substance.

14. The kit of claim 9, wherein at least one of an R group, $R^2$–$R^6$ and Y bear a substituent which improves the solubility of said dioxetane in aqueous solution.

15. A method for detecting a first substance in a sample, comprising adding the compound of claim 1 to said sample, wherein X is removed by said first substance, incubating said sample and inspecting said sample for the generation of light, wherein light so generated is indicative of the presence, and the amount of light detected is indicative of the amount, of said first substance.

16. The method of claim 15, wherein said method further comprises adding an enhancement agent to said sample, to enhance the amount of light detected.

17. The method of claim 15, wherein said light is detected by a CCD camera.

18. The method of claim 16, wherein said enhancement agent is an onium quaternary polymer.

19. The method of claim 18, wherein said method further comprises the addition of an enhancement additive, to improve the enhancement of detected chemiluminescent emission effected by said enhancement agent.

20. The method of claim 15, wherein said first substance is an enzyme.

* * * * *